United States Patent
Blahnik et al.

(10) Patent No.: US 10,194,418 B2
(45) Date of Patent: Jan. 29, 2019

(54) DETERMINATION AND PRESENTATION OF CUSTOMIZED NOTIFICATIONS

(71) Applicant: Apple Inc., Cupertino, CA (US)

(72) Inventors: Jay Kriz Blahnik, San Francisco, CA (US); Aaron P. Thompson, San Francisco, CA (US); David S. Clark, San Jose, CA (US); Julie A. Arney, Los Gatos, CA (US); Brian R. Drell, San Jose, CA (US); Keith P. Avery, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/705,802

(22) Filed: Sep. 15, 2017

(65) Prior Publication Data

US 2018/0352534 A1 Dec. 6, 2018

Related U.S. Application Data

(60) Provisional application No. 62/514,677, filed on Jun. 2, 2017.

(51) Int. Cl.
*H04W 68/04* (2009.01)
*A63B 24/00* (2006.01)
*H04L 29/08* (2006.01)

(52) U.S. Cl.
CPC ......... *H04W 68/04* (2013.01); *A63B 24/0062* (2013.01); *A63B 24/0075* (2013.01); *H04L 67/26* (2013.01)

(58) Field of Classification Search
CPC ............ A63B 24/0062; A63B 24/0065; A63B 24/0068; A63B 24/0075; A63B 24/0078; A63B 24/0081; H04W 68/04; H04W 4/20; H04L 12/1859; H04L 67/26
See application file for complete search history.

(56) References Cited

U.S. PATENT DOCUMENTS

| | | | |
|---|---|---|---|
| 7,130,664 B1 | 10/2006 | Williams | |
| 7,662,065 B1 | 2/2010 | Kahn et al. | |
| 8,610,582 B2 | 12/2013 | Jeon et al. | |
| 9,329,053 B2 | 5/2016 | Lakovic et al. | |
| 9,662,072 B2 * | 5/2017 | Ohsawa | A61B 5/721 |
| 2002/0039952 A1 * | 4/2002 | Clem | A63B 22/0023 482/8 |

(Continued)

FOREIGN PATENT DOCUMENTS

| | | |
|---|---|---|
| EP | 2 040 211 A1 | 3/2009 |
| EP | 2 770 454 A1 | 8/2014 |

(Continued)

OTHER PUBLICATIONS

Search Report and Written Opinion dated Aug. 21, 2018 in International Application No. PCT/US2018/029985. 14 pages.

*Primary Examiner* — Magdi Elhag
(74) *Attorney, Agent, or Firm* — Kilpatrick Townsend & Stockton LLP

(57) ABSTRACT

Coaching notifications can be determined based on current user fitness data and historical user fitness data. The coaching notifications may include information that encourages or otherwise coaches users towards established fitness goals. To this end, the timing for presenting along with the substance of the coaching notifications can be customized to the users.

20 Claims, 12 Drawing Sheets

(56) References Cited

U.S. PATENT DOCUMENTS

| | | | |
|---|---|---|---|
| 2008/0090703 A1* | 4/2008 | Rosenberg | A63B 24/00 482/8 |
| 2010/0179833 A1* | 7/2010 | Roizen | G06Q 50/10 705/3 |
| 2011/0087076 A1* | 4/2011 | Brynelsen | A61B 5/1118 600/300 |
| 2012/0253485 A1 | 10/2012 | Weast et al. | |
| 2012/0283855 A1 | 11/2012 | Hoffman et al. | |
| 2013/0106684 A1 | 5/2013 | Weast et al. | |
| 2014/0221790 A1* | 8/2014 | Pacione | A61B 5/0022 600/301 |
| 2014/0240122 A1 | 8/2014 | Roberts et al. | |
| 2014/0244009 A1* | 8/2014 | Mestas | A63B 24/0062 700/91 |
| 2014/0273978 A1 | 9/2014 | Van Snellenberg | |
| 2015/0196805 A1* | 7/2015 | Koduri | A63B 24/0087 482/6 |
| 2015/0347689 A1* | 12/2015 | Neagle | G06F 19/3475 705/3 |
| 2016/0029125 A1 | 1/2016 | Armstrong et al. | |
| 2016/0058331 A1* | 3/2016 | Keen | G06F 9/542 600/595 |
| 2016/0077495 A1 | 3/2016 | Brown et al. | |
| 2016/0096074 A1 | 4/2016 | Moll-Carrillo et al. | |
| 2016/0166156 A1 | 6/2016 | Yuen et al. | |
| 2016/0166195 A1 | 6/2016 | Radecka et al. | |
| 2016/0287939 A1* | 10/2016 | Deochand | A63B 24/0062 |
| 2016/0365006 A1* | 12/2016 | Minturn | G09B 5/00 |
| 2017/0100637 A1* | 4/2017 | Princen | A63B 71/0622 |
| 2017/0333755 A1* | 11/2017 | Rider | A63B 24/0075 |

FOREIGN PATENT DOCUMENTS

| | | |
|---|---|---|
| WO | 2016/036486 A1 | 3/2013 |
| WO | 2016/140732 A1 | 9/2016 |

* cited by examiner

DETERMINATION AND PRESENTATION OF CUSTOMIZED NOTIFICATIONS

CROSS-REFERENCE TO RELATED APPLICATION(S)

This application claims the benefit of U.S. Provisional Application No. 62/514,677, filed Jun. 2, 2017, entitled "Determination and Presentation of Customized Notifications," and is related to and incorporates by reference U.S. patent application Ser. No. 14/740,004 filed Jun. 15, 2015 and entitled "Dynamic Rule-Based Notifications."

BACKGROUND

Electronic devices, especially portable electronic user devices, are quickly becoming ubiquitous in every modern society. Such devices often include functionality to schedule future notifications (e.g., reminders of calendar events) and to process unscheduled notifications (e.g., alerts about breaking news or new messages). While such notifications can be useful, when notifications are presented too frequently or with irrelevant information, users may experience alarm fatigue. Alarm fatigue results in users becoming desensitized to the notifications, which can lead to users intentionally ignoring the notifications or otherwise missing them.

Goal setting and goal keeping is an effective way to achieve a desired result. This is especially true when improving one's health is the desired result. Even with established goals, users often get busy with other activities and forget about keeping their goals and/or prioritize other activities ahead of keeping their goals. This can lead to abandonment of goal setting.

BRIEF SUMMARY

Examples of the present disclosure can provide devices, systems, computer-implemented methods, and computer-readable media for determining aspects of user coaching notifications. According to one example, a computer-implemented method is provided. The method may include accessing, by a fitness application of a wearable device having an associated user account, historical fitness data associated with the user account. The historical fitness data may be collected by the wearable device during a plurality of days that together define a historical period. The method may also include detecting a beginning of a current day based at least in part on a detected user action performed at the wearable device. The current day may include a plurality of segments. The method may also include determining whether to present a coaching notification at a conclusion of a first segment of the plurality of segments by at least: accessing current fitness data collected by the wearable device and tracked by the fitness application during the first segment, comparing the current fitness data to the historical fitness data to identify a correlation between a current progress toward a fitness goal and a historical progress toward the fitness goal, and determining, based at least in part on the correlation, whether the fitness goal is achievable during one or more other segments of the plurality of segments. The method may also include presenting a coaching notification at the conclusion of the first segment when the fitness goal is achievable during the one or more other segments. The coaching notification may identify the fitness goal.

According to another example, a wearable electronic device is provided. The wearable device may include a display, a memory configured to store computer-executable instructions, and a processor configured to access the memory and execute the computer-executable instructions. Executing the computer-executable instructions may perform operations including accessing historical fitness data collected during a plurality of periods that together define a historical period. Executing the computer-executable instructions may further perform operations including accessing current fitness data collected during a first segment of a current period. Executing the computer-executable instructions may further perform operations including determining a correlation between a current progress toward a user fitness goal and a historical progress toward the user fitness goal based at least in part on the historical fitness data and the current fitness data. Executing the computer-executable instructions may further perform operations including presenting, at the display, a coaching notification at a conclusion of the first segment when the correlation indicates the user fitness goal is achievable during one or more other segments of the current period.

According to yet another example, a computer-implemented method is provided. The method may include accessing, by a fitness application of a wearable device, historical user fitness data. The historical fitness data may be collected by the wearable device during a plurality of periods that together define a historical period. The method may also include determining an estimated conclusion of a current period based at least in part on the historical fitness data. The method may also include accessing current fitness data collected by the wearable device and tracked by the fitness application during the current period. The method may also include determining, based at least in part on the current fitness data, whether a current fitness value associated with a user fitness goal exceeds a threshold. The method may also include, when the current fitness value exceeds the threshold, determining a coaching notification based at least in part on the current fitness data. The coaching notification may identify the user fitness goal and may include a suggested action for achieving the user fitness goal prior to the estimated conclusion of the current period. The method may also include presenting the coaching notification.

According to yet another example, a wearable electronic device is provided. The wearable device may include a display, a memory configured to store computer-executable instructions, and a processor configured to access the memory and execute the computer-executable instructions. Executing the computer-executable instructions may perform operations including determining a period that a wearable device is in a worn state based at least in part on earlier periods of historical data representing the wearable device worn state. Executing the computer-executable instructions may further perform operations including determining, based on configuration information, one or more clock times occurring during the period. Executing the computer-executable instructions may further perform operations including determining when to present a coaching notification by at least: identifying a time window that includes a first clock time of the one or more clock times, identifying an open segment within the time window based at least in part on user calendar data that is descriptive of a calendar associated with a user account, and determining whether a user activity level is within an activity threshold based at least in part on activity data. Executing the computer-executable instructions may further perform operations including presenting, at the display, the coaching notification during the open segment when the activity level is within the activity threshold.

DETAILED DESCRIPTION

Figure 1:
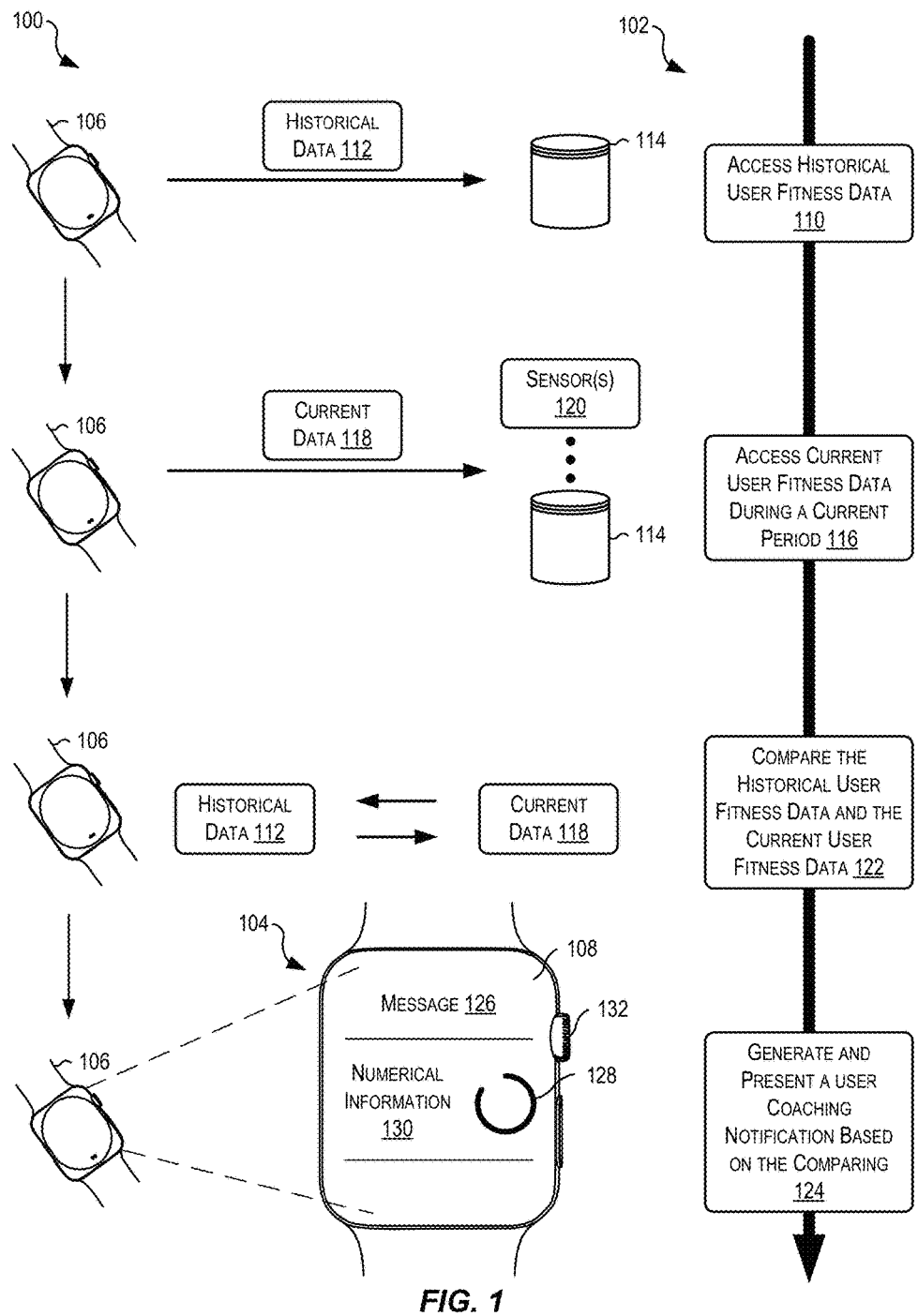
FIG. 1 illustrates a simplified block diagram depicting an example flowchart for determining aspects of user coaching notifications, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, devices, and computer-readable media for determining appropriate timing and substance of notifications for presentation at user devices. These determinations along with presentation of the notifications can be performed in a manner that is customized to users associated with the user devices. Unlike less sophisticated approaches, notifications presented using techniques described herein may do little to contribute to alarm fatigue. This may be because timing and notification customization is determined using particular sets of rules and triggers that consider historical data associated with the users, biometric data of the users, real-time data associated with the users, and other relevant data. In this manner, the timing and substance of the notifications may adjust to conditions of a current period and a given historical period. For example, during a first day, a first notification may be presented at a first time and include a first message. During a second day, a second notification may be presented at a second time and include a second message. Thus, the timing of presentation and the substance of the notifications are tuned to ensure that the notifications include relevant information and are presented at appropriate times. Techniques described herein may be performed by an electronic device such as a wearable device, a mobile phone, or other comparable electronic device.

In a particular example, a particular type of notification such as user coaching notifications can reference established user fitness goals (e.g., a stand goal, a move goal, a caloric burn goal, and other similar fitness goals), which may be stored in association with a user account. The user fitness goals may be reset according to some period (e.g., daily, weekly, etc.). The user coaching notifications can be presented at a wearable electronic device at fixed intervals throughout the period based on determinations that the user fitness goals are still achievable during the period. For example, the user coaching notifications may be presented in a manner that is considerate of user progress towards the user fitness goals as compared to historical user progress for other periods (e.g., the last thirty days). The substance of the user coaching notifications may depend on the user progress as compared to the historical user progress. For example, when a user is on pace to achieve a user fitness goal, a user coaching notification may inform the user that she is on pace. When the user is off pace (e.g., behind where she usually is at a given point in time during the day), the user coaching notification may inform the user that she is behind. In both scenarios, the user coaching notification may include a suggestion for achieving the fitness goal. For example, if the user fitness goal is a daily caloric burn goal, the suggestion may indicate an activity (e.g., a brisk walk) and duration for participating in the activity (e.g., 12 minutes) that will allow the user to achieve the daily caloric burn goal. This activity and/or duration may be computed based on biometric data (e.g., height, weight, gender, and/or other similar data) associated with the user account. The user coaching notifications may also reference and coach users towards user breathing goals. For example, if the user were to establish a goal to conduct a breathing exercise three times a day, the techniques described herein can track this goal and identify appropriate times for presenting user coaching notifications about the breathing goal.

FIG. 1 illustrates a simplified block diagram 100 depicting an example process 102 for determining aspects of user coaching notifications 104, according to at least one example. The diagram 100 includes a wearable electronic device 106 that includes a display 108 on which is displayed an example user coaching notification 104. The wearable electronic device 106 can be any suitable electronic device capable of collecting (e.g., via one or more sensors) and tracking (e.g., via a fitness application) user fitness data and presenting the user coaching notifications 104 when the wearable electronic device 106 is in a worn state. In some examples, the function of collecting and tracking user fitness data and presenting the user coaching notifications 104 is split between two or more electronic devices. For example, the wearable electronic device 106 may collect user fitness data and a user device (e.g., a smartphone) may track the user fitness data and determine matters relating to presenting the user coaching notifications 104.

The process 102 may begin at 110 by accessing historical user fitness data 112. This may be performed by the wearable electronic device 106. The historical user fitness data 112 may be associated with a user account of a user of the wearable electronic device 106. The historical user fitness data 112 may be accessed from a database 114. The database 114 may be local to the wearable electronic device 106, may include data replicated from a similar database stored at a remote location, and/or may be accessed by the wearable electronic device 106 from the remote location. In some examples, the historical user fitness data 112 stored in the database 114 may correspond to some fixed amount of time (e.g., a week, a month, a year, etc.) and may be organized based on some period of the fixed amount of time (e.g., day, week, month, etc.). For example, the historical user fitness data 112 may constitute a month's worth of data organized by each day in the month. In some examples, the historical user fitness data 112 may represent a user profile of the user of the wearable electronic device 106.

At least a portion of the process 102 may be performed at the beginning of each period, when it is first detected that the wearable electronic device 106 is in a worn state. For example, when the user first puts on the wearable electronic device 106 in the morning, the process 102 may be triggered for performance. As described herein, different approaches may be implemented to detect when the user first puts on the wearable electronic device 106. In any event, because the process 102 may be performed periodically and the wearable electronic device 106 continues to collect user fitness data, the historical user fitness data 112 that is accessed may be different each time the process 102 is performed.

At 116, the process 102 may include accessing current user fitness data 118 during a current period. This may be performed by the wearable electronic device 106. The current user fitness data 118 may be associated with the user account of the user of the wearable electronic device 106. The current fitness data 118 is considered "current" because it is collected during the current period. For example, if the period were a day, the current fitness data 118 may include data collected while the wearable electronic device 106 is in a worn state during the day.

The current user fitness data 118 may be accessed from the database 114, from one or more sensors 118, and/or from any other suitable data structure or collection device. In some examples, the one or more sensors 120 are included in the wearable electronic device 106 and are used to collect the current user fitness data 118. In some examples, the current user fitness data 118 is collected by the one or more sensors 120 and added to the database 114. For example, the one or more sensors 120 may collect the current user fitness data 118 continuously when the wearable electronic device 106 is in the worn state, periodically based on events detected at the wearable electronic device 106 (e.g., when the wearable electronic device 106 is in the worn state and an activity mode is selected on the wearable electronic device 106), and/or in any other suitable manner.

After the period has expired in which the current user fitness data 118 was collected (e.g., at the end of the day), the current user fitness data 118 may be considered historical user fitness data 112.

At 122, the process 102 may include comparing the historical user fitness data 112 and the current user fitness data 118 to determine whether certain notification rules and/or conditions are met. This may be performed by the wearable electronic device 106. This comparison may be used to determine a current user progress towards a user fitness goal as compared to previous periods. For example, using the historical user fitness data 112, an average period length can be determined (e.g., 15 hours). Again, using the historical fitness data 112, the average period length can be divided up into a set of intervals (e.g., quarters, thirds, halves, etc.). The intervals can be equivalent or may not be equivalent. In any event, at each interval, the process 102, or at least a portion thereof, may be performed to determine how the user is progressing towards the user fitness goal based how the user has performed in the past.

In some examples, the historical user fitness data 112 may be processed to determine a profile for the user and/or a model of the user. The profile and/or model may indicate at which portions during the period the user typically performs activities toward achieving her goals. If it is known that the user generally works out in the evening, e.g., based on the profile and/or model, it may be less of a concern that at noon the user has only achieved 20% of her goal. In this manner, the historical fitness data 112 may represent a track record for the user (e.g., even though she is behind early in the day, she typically makes the difference). This approach may also consider the day of the week. For example, the historical user fitness data 112 can be processed to determine, for each day of a historical period, at which portions during each day the user typically performs activities towards achieving her goals. For example, the user may workout in the morning during the week, but workout in the evenings on the weekend.

At 124, the process 102 may include generating and presenting the user coaching notification 104 based on the comparing performed at 122. This may be performed by the wearable electronic device 106. In particular, the user coaching notification 104 may be generated based on the user's progress towards the user fitness goal (determined by the comparing), the particular interval, and details about the user fitness goal. In some examples, the user coaching notification 104 may include a message 126, graphical indicator 128, and/or numerical information 130. The substance of the message 126 may be varied based on the user's progress (e.g., whether the user is behind her goals, ahead of her goals, and/or on pace). The graphical indicator 128 may graphically indicate the user's progress toward the user fitness goal. The numerical information 130 may constitute a numerical representation of the user's progress toward the user fitness goal (e.g., 350 calories out of 400).

In some examples, other user coaching notifications 104 that have been generated may be viewed on the display 108 by adjusting an input component 132 (e.g., scrolling down). This adjustment may reveal other user coaching notifications 104 that may correspond to other user fitness goals.

In some examples, after presentation of the user coaching notifications 104, a user input may be received that causes the wearable electronic device 106 to change to an activity mode. In the activity mode, the wearable electronic device 106 may collect fitness data more frequently and/or in a different manner than in other modes. For example, the activity mode may include a set of activities or workouts that can be selected by the user. Depending on the selection of an activity or workout, the wearable electronic device 106 may collect and process fitness data in a particular manner.

In some examples, the graphical indicator 128 may be part of an updatable graphical fitness user interface element. The updateable graphic fitness user interface element may include one or more concentric rings. Each concentric ring may represent a particular aspect of the current fitness data of the user of the wearable electronic device 106. In this manner, the updatable graphical fitness user interface element may function as an activity indicator to provide a graphical representation of the extent to which the user has been "active" as compared to goals relating to physical activity. For example, an outer ring may represent an caloric burn goal (e.g., a daily number of active Calories expended), a center ring may represent a move goal (e.g., a daily number of minutes spent performing physical activity above a physical activity threshold (e.g., an intensity above a brisk walk or 3 metabolic equivalent units (METS))), and an inner ring may represent a stand goal (e.g., a number of hours in the day during which the user stood for at least 60 seconds within a 90 second segment of time). As the user performs more physical activities and thereby gets closer to achieving their goals, the concentric rings will continue to close. Thus, a closed ring, may correspond to an achieved goal for that physical activity. Thus, the graphical indicator 128 may represent current progress toward the goal (e.g., a completed ring).

In some examples, the techniques described herein may improve the functioning of the wearable electronic device 106 and/or other computing devices by reducing the computing resources required for presentation of notifications. This may be partly because fewer notifications are determined and presented as compared to other approaches.

Figure 2:
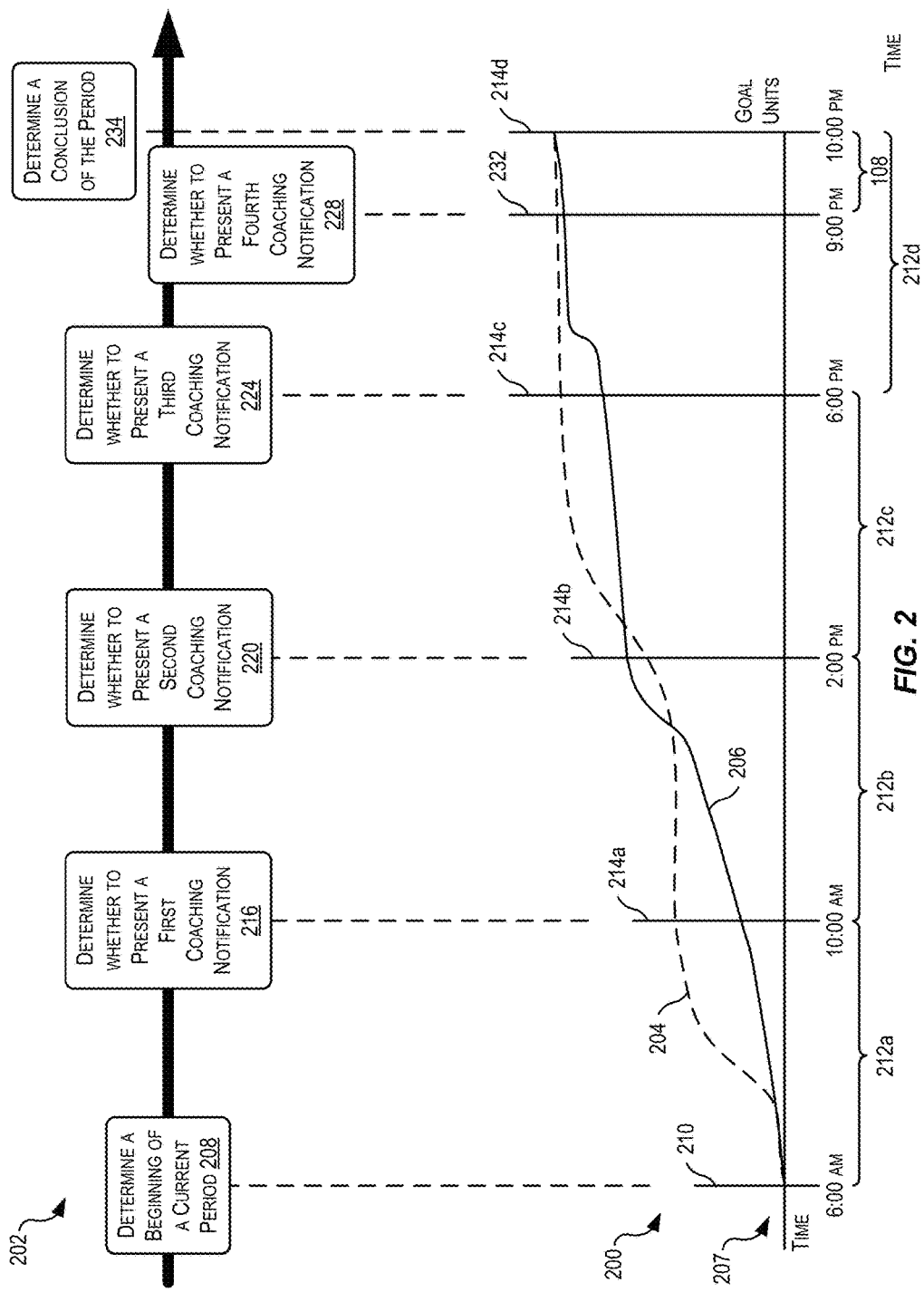
FIG. 2 illustrates an example user activity graph together with an example flowchart for determining aspects of user coaching notifications, according to at least one example.

FIG. 2 illustrates an example user activity graph 200 together with an example flow illustrating a process 202 for determining aspects of user coaching notifications, according to at least one example. The process 202 may be performed by the wearable electronic device 106 or other comparable device, as described herein.

The user activity graph 200 may, for one period such as day, illustrate the historical user fitness data 112 and the current user fitness data 118 respectively as historical line 204 and current line 206. In particular, the historical line 204 may represent, as an average, how the user has achieved goal units (e.g., calories, activity minutes, repetitions, miles, etc.). For example, the historical line 204 may represent the user's progress toward her goal of having 30 per day workout minutes during multiple days prior to the current day. Similarly, the current line 206 may represent how the user is currently achieving goal units (e.g., is currently progressing towards her goal of 30 workout minutes) during a current period (e.g., day) 207. The user activity graph 200 includes a complete current line 206 which indicates that the current period 207 has been completed. It should be understood, however, that at least some of the coaching notifications described herein may be presented at intervals prior to conclusion of the current period 207.

The process 202 may begin at 208 by determining a beginning 210 of the current period 207. This may be performed by the wearable electronic device 106. Determining the beginning 210 of the current period 207 may include detecting a user action that is indicative of the beginning 210 of the current period 207. For example, the user may put on the wearable electronic device 106 and input an access code on the wearable electronic device 106 and/or pair the wearable electronic device 106 with a different electronic device. Either of these actions or some other action may be detected and correlated to the beginning 210 of the current period 207. In some examples, the current period 207 begins when the wearable electronic device 106 first collects user fitness data after having not collected user fitness data for an extended period of time (e.g., while the user is asleep). The current period 207 may also begin based on a clock time. For example, the beginning 210 of the current period 207 may begin at 6:00 am each day (e.g., corresponding to a user's wake time).

In some examples, an estimated length of the current period 207 is determined based on the historical user fitness data 118. For example, an average clock time for a conclusion of the historical time periods can be used as an estimated conclusion of the current period 207. The estimated length of the current period 207 may be measured from the beginning 210 to the estimated conclusion. In this example, the beginning 210 may be 6:00 am and the estimated conclusion may be 10:00 pm (e.g., when the user takes the wearable device 106 off in preparation for sleep). Thus, the estimated length of the current period 207 may be 16 hours.

The current period 207 may be divided into one or more intervals 212a-212d, which may be fixed, variable, uniform, non-uniform, and/or have any other suitable characteristic. For example, the estimated length may be divided into equal fourths. Thus, a first conclusion 214a of the first interval 212a may correspond to 10:00 am or 25% of the current period 207, a second conclusion 214b of the second interval 212b may correspond to 2:00 pm or 50% of the current period 207, a third conclusion 214c of the third interval 212c may correspond to 6:00 pm or 75% of the current period 207, and a fourth conclusion 214d of the fourth interval 212d may correspond to 10:00 pm or 100% of the current period 207.

Figure 3:
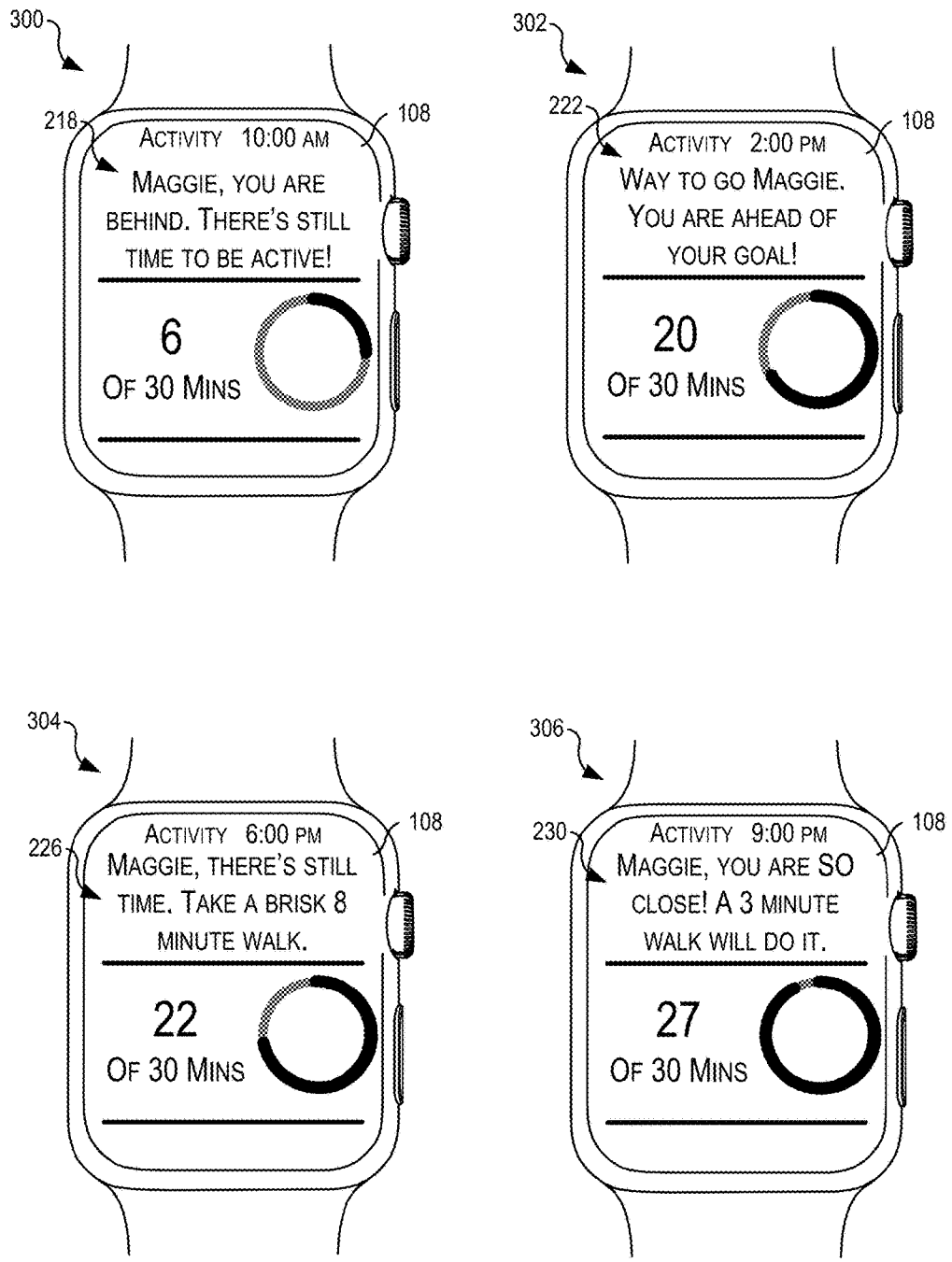
FIG. 3 illustrates example views of a user coaching graphical user interface including user coaching notifications, according to various examples.

At 216, the process 200 may include determining whether to present a first coaching notification 218. This may be performed by the wearable electronic device 106 at the first conclusion 214a of the first interval 212a. FIG. 3 illustrates an example of the first coaching notification 218 in a first view 300 of a user coaching graphical user interface that is presented at the display 108. Determining whether to present the first coaching notification 218 may include comparing historical user progress with current user progress as represented by historical line 204 and the current line 206. Historically, at the first conclusion 214a, the user has already achieved around 15 activity minutes. For example, historically the user may have a 15 minute bike ride to work in the morning. This may result in the 15 activity minutes being recorded by the wearable electronic device 106. Thus, historically the wearable electronic device 106 may collect more activity minutes during the first interval 212a than in the current period. For example, during the first interval 212a of the current period 207, the user may have ridden the bus to work, which resulted in fewer activity minutes being collected by the wearable electronic device 106.

In some examples, the first coaching notification 218 and/or other coaching notifications may not be presented at the wearable electronic device 106, even though Maggie is behind on her goal. For example, if the historical user fitness data 112 indicates that Maggie is still likely to achieve her goal during the remainder of the current period 207 (e.g., has a track record of catching up, despite how far behind she is at the current time), the process 200 may refrain from sending any coaching notifications. If, however, the historical user fitness data 112 indicates that Maggie is unlikely to achieve her goal during the remainder of the current period 207 (e.g., has a track record of not catching up given how far behind she is and the current time), the process 200 may present the first coaching notification 218 as described herein.

The first coaching notification 218 may be customized based on the user status at the first conclusion 214a. For example, the first coaching notification 218 may include an example motivational message that informs the user, Maggie, that her progress is lagging, but that her fitness goal is still achievable during the current period 207 (e.g., "Maggie, you are behind. There's still time to be active!"). The first coaching notification 218 may also identify numerically the number of activity minutes achieved and the goal (e.g., "6 out of 30 mins"). Finally, the first coaching notification 218 may also identify graphically the number of activity minutes as a portion of the goal (e.g., a segment of a circle). The issuance of this coaching notification is based on the determination that at this point in time, Maggie's goal is still achievable based at least on her historical performance and on the amount of time left in the current period 207.

At 220, the process 200 may include determining whether to present a second coaching notification 222. This may be performed by the wearable electronic device 106 at the second conclusion 214b of the second interval 212b. FIG. 3 illustrates an example of the second coaching notification 222 in a second view 302 of a user coaching graphical user interface that is presented at the display 108. Determining whether to present the second coaching notification 222 may include comparing historical user progress with current user progress as represented by historical line 204 and the current line 206. Historically, at the second conclusion 214b, the user has already achieved around 18 activity minutes. For example, historically the user may have meetings during the second interval 212b, which result in the user not collecting very many activity minutes during the second interval 212b. This may result in only a few activity minutes being recorded by the wearable electronic device 106 during the second interval 212b. During the second interval 212b of the current period 207, however, the user may have gone for a brisk walk or worked out in the gym, which resulted in more activity minutes being collected by the wearable electronic device 106 than historically collected during the second interval 212b. Thus, at the second conclusion 214b of the second interval 212b, the user has more activity minutes than she historically has (e.g., 20 vs. 18).

The second coaching notification 222 may be customized based on the user status at the second conclusion 214b. For example, the second coaching notification 222 may include an example motivational message that informs the user, Maggie, that she is currently ahead of her historical progress (e.g., "Way to go Maggie. You are ahead of your goal!"). The second coaching notification 222 may also identify numerically the number of activity minutes achieved and the goal (e.g., "20 out of 30 mins"). Finally, the second coaching notification 222 may also identify graphically the number of activity minutes as a portion of the goal (e.g., a segment of a circle).

At 224, the process 200 may include determining whether to present a third coaching notification 226. This may be performed by the wearable electronic device 106 at the third conclusion 214c of the third interval 212c. FIG. 3 illustrates an example of the third coaching notification 226 in a third view 304 of a user coaching graphical user interface that is presented at the display 108. Determining whether to present the third coaching notification 226 may include comparing historical user progress with current user progress as represented by historical line 204 and the current line 206. Historically, at the third conclusion 214c, the user has already achieved around 29 activity minutes. For example, historically the user may ride her bike home from work resulting in collection of many activity minutes during the third interval 212c. During the third interval 212b of the current period 207, however, the user may have stayed late at work, have been on a plane, or have done something else which resulted in fewer activity minutes being collected by the wearable electronic device 106 than historically collected during the third interval 212c. Thus, at the third conclusion 214c of the third interval 212c, the user has fewer activity minutes than she historically has (e.g., 22 vs. 29).

The third coaching notification 226 may be customized based on the user status at the third conclusion 214c. For example, the third coaching notification 226 may include an example motivational message that informs the user, Maggie, that she is currently behind her historical progress, and includes a suggestion for achieving her fitness goal (e.g., "Maggie, there's still time. Take a brisk 8 minute walk."). Given the current time, the fitness goal of 30 activity minutes may still be achievable by the user (e.g., current period includes more than 8 minutes).

The suggested activity in this example is a brisk walk. In some examples, the suggested activity may be any suitable activity that is related to the user fitness goal such as one that causes the user's heart rate to exceed some threshold; thus, resulting in the wearable electronic device 106 recording the time spent on the activity towards the activity minutes goal. In some examples, the suggested activity may be determined using a calorimetric computation based on a biometric data of the user. For example, when the user fitness goal includes a quantity of activity calories (e.g., calories burned at an elevated heart rate), the biometric data of the user may be used to determine the activity and the number of minutes or repetitions (e.g., 11 minute brisk walk, 5 minute jog, 7 minute bike ride, 15 jumping jacks, 50 push-ups, 5 burpees, etc.) that, if completed, will accomplish the user fitness goal.

The third coaching notification 226 may also identify numerically the number of activity minutes achieved and the goal (e.g., "22 out of 30 mins"). Finally, the third coaching notification 226 may also identify graphically the number of activity minutes as a portion of the user fitness goal (e.g., a segment of a circle).

At 228, the process 200 may include determining whether to present a fourth coaching notification 230 during one of the intervals 212 at a threshold time 232. This may be performed by the wearable electronic device 106. In some examples, the fourth coaching notification 230 may be considered a threshold coaching notification at least because it may be based on the threshold time 232 and/or a threshold completion value. FIG. 3 illustrates an example of the fourth coaching notification 230 in a fourth view 306 of a user coaching graphical user interface that is presented at the display 108.

Determining whether to present the fourth coaching notification 230 may include comparing historical user progress with current user progress as represented by historical line 204 and the current line 206. In some examples, the fourth coaching notification 230 may be presented at or near a fourth conclusion 214d of the fourth interval 212d. The fourth conclusion 214d may correspond to the estimated conclusion of the current period 207. The timing of the threshold time 232 may be selected to be some fixed value prior to the estimated conclusion of the current period 207 (e.g., 1 hour, 2 hours, 3 hours, etc.). In some examples, the fourth coaching notification 230 is generated and presented when the user is close to achieving her fitness goal. For example, to avoid the circumstance where the user misses her fitness goal by only a small amount, if the user is within some threshold value of achieving her fitness goal (e.g., 10%) at the threshold time 232, the fourth coaching notification 230 may be generated and presented. Thus, in this example, historically, at the threshold time 232, the user has all but achieved her fitness goal. However, in the current period 207, the user may be slightly behind and risks not achieving her fitness goal for the current period 207. Thus, presentation of the fourth coaching notification 230 may assist the user in achieving her goals.

In some examples, determining whether to present the fourth coaching notification 230 may include, at a fixed time prior to the fourth conclusion 214d (e.g., 1 hour, 2 hours, 3 hours, etc.), determining how much is left for the user to achieve her goal (e.g., 10 more minutes of exercise, 50 more calories to burn, etc.) based on the current fitness data 118 and how much the user typically gets between the fixed time and the fourth conclusion 214d on an average day based on the historical fitness data 112. If it is likely (e.g., a 50% or greater likelihood), given this comparison of the current fitness data 118 and the historical fitness data 112, that the user will achieve her goal, the process 200 may refrain from presenting the fourth coaching notification 230. This may be because the user is likely to achieve her goal without being prompted. If, however, it is unlikely (e.g. a 49% or lower likelihood), given this comparison of the current fitness data 118 and the historical fitness data 112, that the user will achieve her goal, the process 200 may present the fourth coaching notification 230. In this example, this may be based not on a likelihood of catching up, but on a likelihood that the amount of time remaining allows would allow the user to achieve her goal.

The fourth coaching notification 230 may be customized based on the user status at the threshold time 232. For example, the fourth coaching notification 230 may include an example motivational message that informs the user, Maggie, that she is close to achieving her goal, and includes a suggestion for achieving her goal (e.g., "Maggie, you are so close! A 3 minute walk will do it."). Thus, like the third coaching notification 226, the fourth coaching notification 230 may inform the user of her status and suggest an activity for accomplishing her goal.

The fourth coaching notification 230 may also identify numerically the number of activity minutes achieved and the goal (e.g., "27 out of 30 mins"). Finally, the fourth coaching notification 230 may also identify graphically the number of activity minutes as a portion of the goal (e.g., a segment of a circle).

At 234, the process 200 may include determining a conclusion of the period. This may include determining the conclusion of the current time period 207, which may correspond to the fourth conclusion 214d. In some examples, determining the conclusion of the period includes estimating a clock time when the wearable electronic device 106 is no longer collecting user fitness data or is unlikely to collect any additional user fitness data. In some examples, the conclusion of the period corresponds to a period in which the wearable electronic device 106 no longer collects certain user fitness data above some threshold. For example, the wearable electronic device 106 may collect calorie data every 15 minutes in a normal operation mode, but if two 15-minute periods pass and no calorie data is collected, the wearable electronic device 106 may identify a time associated with the two 15-minute periods as the conclusion of the period. In some examples, the conclusion of the period may also correspond to an estimated time after which the user is unlikely to perform actions towards achievement of their fitness goals based on historical user fitness data.

FIGS. 4, 5, 6, and 7 illustrate example flow diagrams showing processes 400, 500, 600, and 700 for determining aspects of user coaching notifications, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

Figure 4:
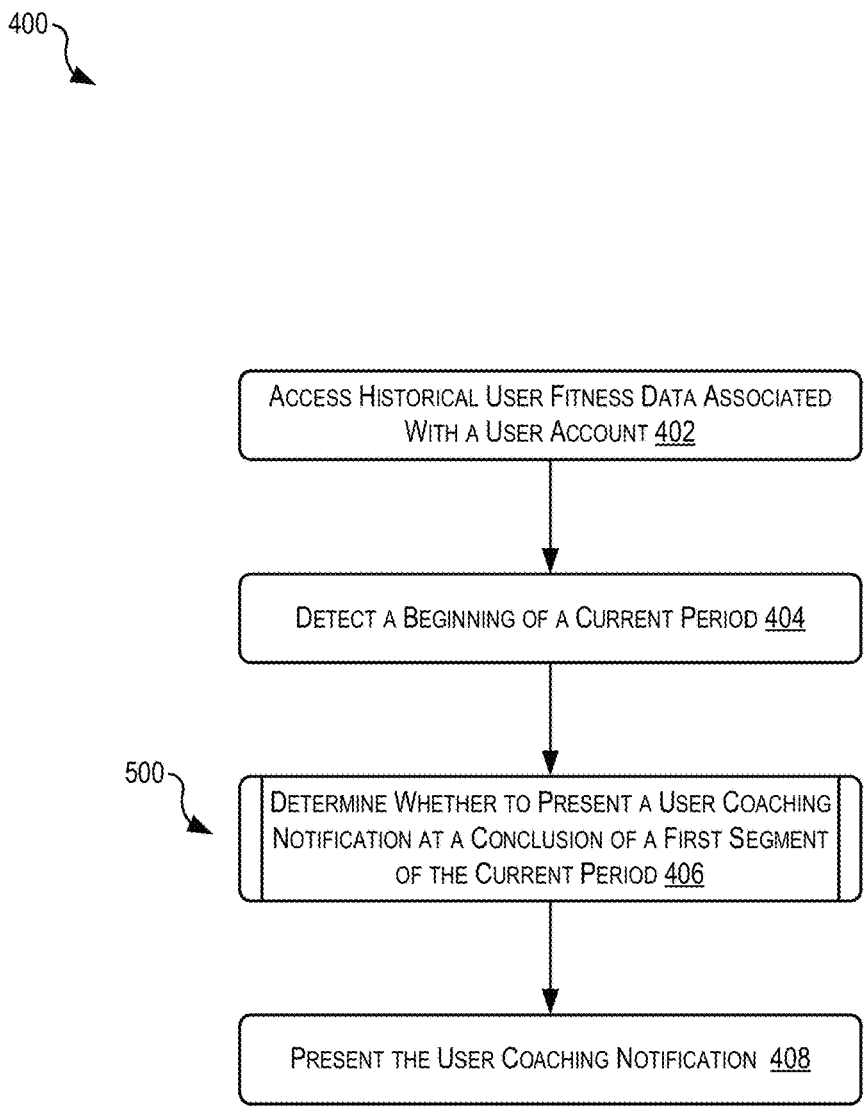
FIG. 4 illustrates a flowchart of a process for determining aspects of user coaching notifications, according to at least one example.

FIG. 4 depicts the process 400 including example acts or techniques relating to determining aspects of user coaching notifications, according to at least one example. A fitness module 810, whether embodied in the wearable electronic device 106, a user device 802, or a service provider computer 804, or any suitable combination of the foregoing may perform the process 400 of FIG. 4. The process 400 may begin at 402 by accessing historical user fitness data associated with a user account. In some examples, accessing historical user fitness data may be performed by a fitness application of a wearable device associated with the user account. The historical fitness data may be collected by the wearable device during a plurality of periods that together define a historical period. For example, a single period of the plurality of periods may correspond to a day and the historical period may correspond to a month. In some examples, the historical fitness data has been collected while the wearable device is in a worn state.

At 404, the process 400 may include detecting a beginning of a current period. This may be based at least in part on a detected user action performed at the wearable device. For example, the user input may include a code or action performed by a user at the wearable device. For example, when the user first puts the wearable device on in the morning, she may input an unlock code at the display of the wearable device. In some examples, the current period may include or be defined by a plurality of segments. In some examples, each segment of the plurality of segments is equivalent.

At 406, the process 400 may include determining whether to present a user coaching notification at a conclusion of a first segment of the first current period (e.g., a first segment of the plurality of segments). Block 406 is discussed in more detail with reference to FIG. 5. In some examples, the coaching notification indicates a current user progress toward a fitness goal. The fitness goal may include at least one of a stand goal, an caloric burn goal, a move goal, and/or any other suitable fitness-related goal.

At 408, the process 400 may include presenting the user coaching notification. In some examples, the user coaching notification is presented at the conclusion of the first segment when the fitness goal is achievable during one or more other, later segments. The user coaching notification may identify the user fitness goal.

In some examples, the coaching notification may include an option for beginning a workout. In this example, the process 400 may further include receiving information indicating user selection of the option. The process 400 may further include, in response to receiving the information, initiating the workout. The process 400 may further include collecting additional current fitness data during the workout.

In some examples, the process 400 may further include determining an estimated conclusion of the current period based at least in part on the historical fitness data. In this example, the coaching notification may include a suggested action that, if performed prior to the estimated conclusion of the period, may result in the user achieving the fitness goal prior to the estimated conclusion of the current period.

In some examples, the process 400 may further include determining an estimated conclusion of the current period based at least in part on the historical fitness data. The process 400 may further include determining, based at least in part on the current fitness data, whether a current fitness value (e.g., number of calories burned, number of activity minutes, etc.) associated with the user fitness goal exceeds a threshold. The process 400 may further include, when the current fitness value exceeds the threshold, determining a second coaching notification based at least in part on the current fitness data. In some examples, the second coaching notification may identify the user fitness goal and may include a suggested action for achieving the user fitness goal prior to the estimated conclusion of the current period. In some examples, the second coaching notification may be further based at least in part on user biometric information.

Figure 5:
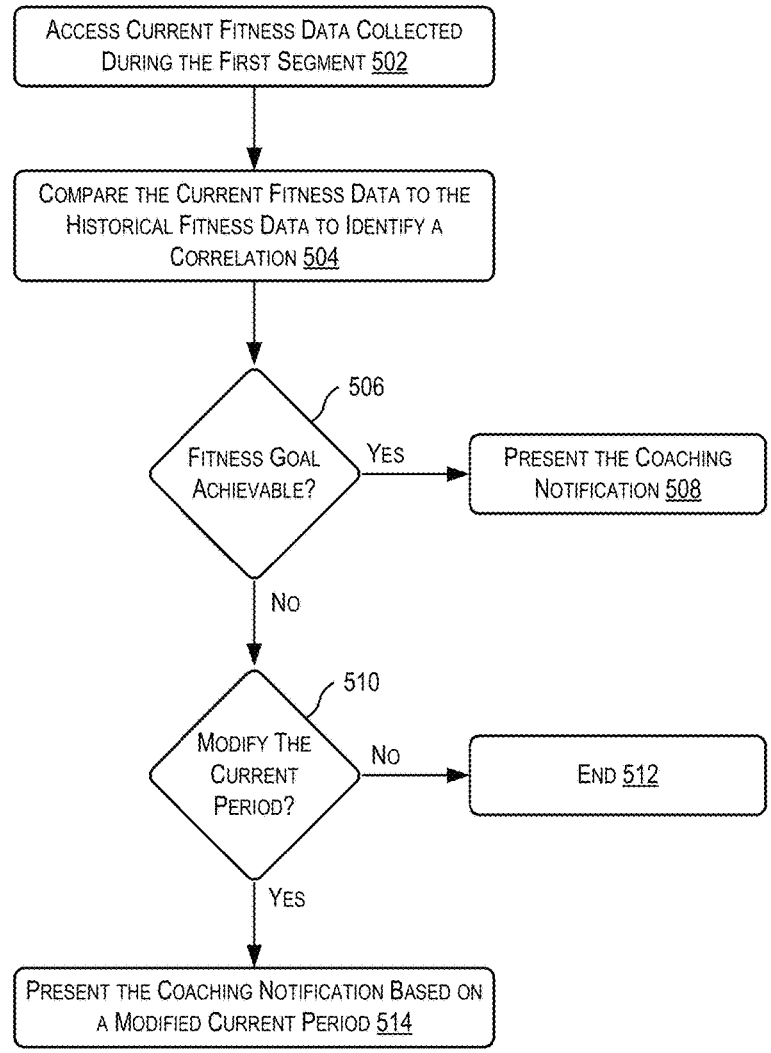
FIG. 5 illustrates a flowchart of a process for determining aspects of user coaching notifications, according to at least one example.

FIG. 5 depicts the process 500 including example acts or techniques relating to determining aspects of user coaching notifications, according to at least one example. The fitness module 810 (FIG. 8), whether embodied in the wearable electronic device 106 (FIG. 1), the user device 802 (FIG. 8), or the service provider computer 804 (FIG. 8), or any suitable combination of the foregoing may perform the process 500 of FIG. 5. The process 500 may begin at 502 by accessing current fitness data collected during the first segment of the plurality of segments that make up the period from FIG. 4. The data may be collected by the wearable electronic device and tracked by a fitness application executing on the wearable electronic device. For example, the fitness module 810 may be embodied in the fitness application.

At 504, the process 500 may include comparing the current fitness to the historical fitness data to identify a correlation. The correlation may be a correlation between a current progress toward a fitness goal and a historical progress toward the fitness goal. In this manner, the correlation may represent, at a given time, how the user is currently progressing toward her fitness goal as compared to how she has done in the past. With this correlation or other data that is representative of the comparison, a customized and targeted coaching notification can be determined for the user. For example, if the user is ahead of where she typically is, the coaching notification may include a congratulatory message. If the user is behind where she typically is, the coaching notification may include an encouraging message.

At 506, the process 500 may include determining whether the fitness goal is achievable. Determining whether the fitness goal is achievable may include determining based at least in part on the correlation. The fitness goal may be achievable if, given the amount of time left in the period, the user's current progress, and the user's historical progress, the user can still achieve her goal. In some examples, determining whether the fitness goal is achievable may include a basic comparison of the time left in the period and the time required or likely required to achieve the goal. For earlier segments such as 25% completion and 50% completion, it is more likely that the answer at 506 will be yes than for later segments such as 75% completion. This is simply because, for the earlier segments, there is more time left in the period for the user to make up deficits.

If the answer at 506 is yes, the process 500 may proceed to block 508 at which the process 500 may include presenting the coaching notification. In some examples, presenting the coaching notification at 508 may be performed in a similar manner as described with reference to block 408.

If the answer at 506 is no, the process 500 may proceed to block 510 at which the process 500 may include determining whether to modify the current period. This may include determining whether to suggest to the user that the current period be extended in order to give the user additional time to work towards a fitness goal. For example, if the user still needs to stand and move around during two more hours to reach a stand goal and the current period will end in one hour, the determination at 510 may result in the current period being extended for the user to stand during the second hour. In some examples, the determination at 510 may consider the extent of the modification and the probability that the user will actually achieve the fitness goal given the modified period. For example, when the extent of the modification is low and the likelihood is high, the answer at 510 is likely yes. If, however, the extent of the modification is great and the likelihood is low, the answer at 510 is likely no.

If the answer at 510 is no, the process 500 may proceed to block 512 at which the process 500 may end.

If the answer at 510 is yes, the process 500 may proceed to block 514 at which the process 500 may include presenting the coaching notification based on a modified current period. In some examples, presenting the coaching notification at 514 may be performed in a similar manner as described with reference to block 408.

Figure 6:
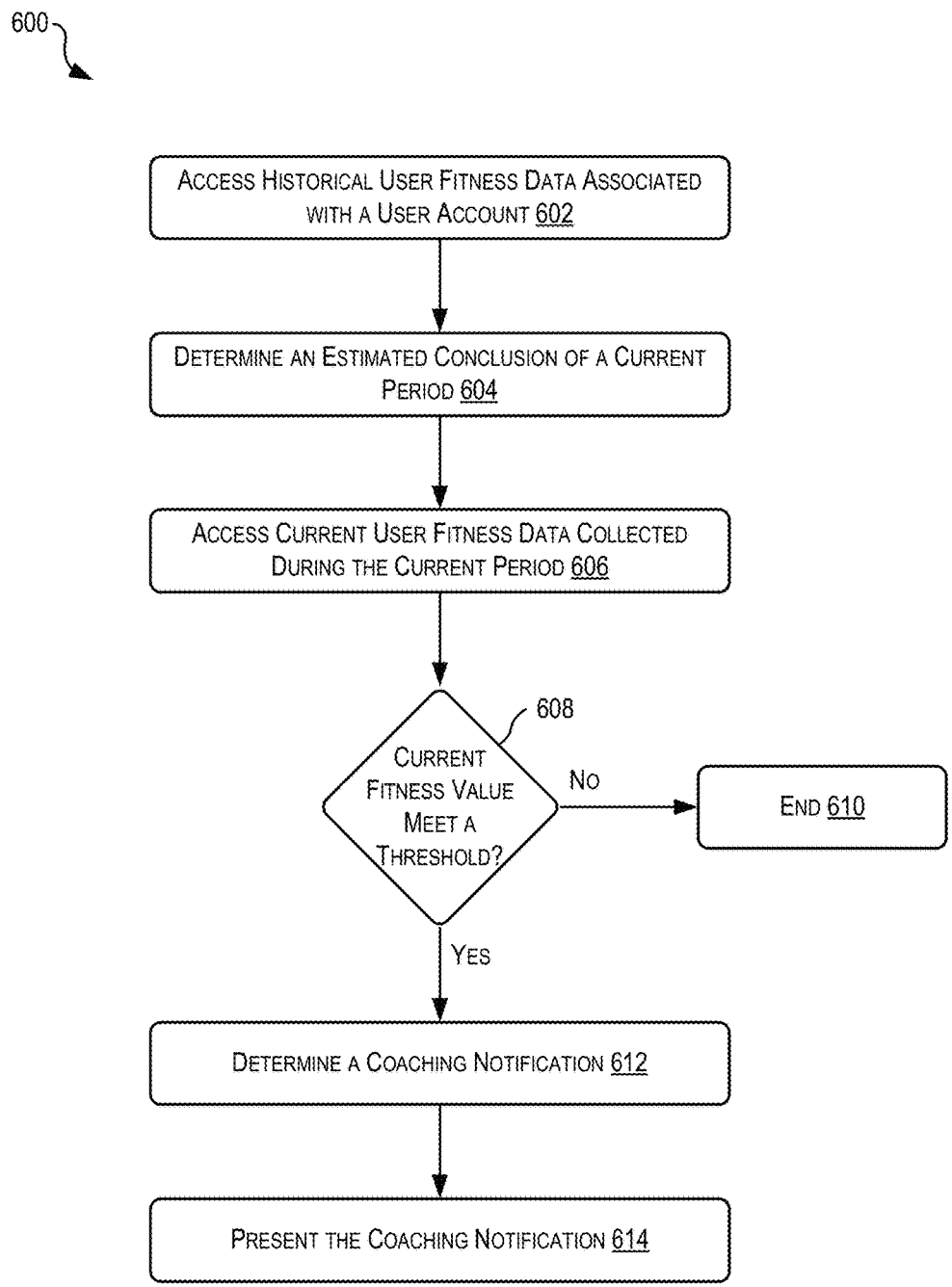
FIG. 6 illustrates a flowchart of a process for determining aspects of user coaching notifications, according to at least one example.

FIG. 6 depicts the process 600 including example acts or techniques relating to determining aspects of user coaching notifications, according to at least one example. The fitness module 810, whether embodied in the wearable electronic device 106, the user device 802, or the service provider computer 804, or any suitable combination of the foregoing may perform the process 600 of FIG. 6. The process 600 may begin at 602 by accessing historical user fitness data associated with a user account. In particular, a fitness application of the wearable electronic device may access the historical user fitness data. The historical fitness data may be collected by the wearable device during a plurality of periods that together define a historical period.

At 604, the process 600 may include determining an estimated conclusion of a current period. In some examples, determining the estimated conclusion may be based at least in part on the historical fitness data.

At 606, the process 600 may include accessing current fitness data collected during the current period. In particular, the current fitness data may be tracked by the fitness application during the current period.

At 608, the process 600 may include determining whether a current fitness value meets a threshold. This determination may be based at least in part on the current fitness data. For example, this determination may include determining whether the current fitness data meets, exceeds, and/or falls below the threshold. For example, the current fitness data may indicate that a user is within 10% of achieving a fitness goal. The current fitness value may be an cumulative value based on the day. For example, if the fitness goal related to calories burned, the current fitness value may be the number of calories the user has burned during the current period as of a particular time in the current period.

If the answer at 608 is no, the process 600 may proceed to 610 at which the process 600 may end.

If the answer at 608 is yes, the process 600 may proceed to 612 at which the process 600 may determine a coaching notification. The coaching notification may be based at least in part on the current fitness data. The coaching notification may identify the user fitness goal and may include a suggested action for achieving the user fitness goal prior to the estimated conclusion of the current period.

At 614, the process 600 may include presenting the coaching notification.

In some examples, the process 600 may further include determining whether the user fitness goal is achievable within a remaining portion of the current period. In this example, determining the coaching notification may include determining the coaching notification when the user fitness goal is achievable within the remaining portion of the current period.

In some examples, the coaching notification may be a threshold coaching notification. In this example, the process 600 may further include comparing the current fitness data to the historical fitness data to identify a correlation between a current progress toward the user fitness goal and a historical progress toward the user fitness goal. The process 600 may further include determining, based at least in part on the correlation, whether the user fitness goal is achievable during the current period. The process 600 may further include, prior to presenting the threshold coaching notification, presenting a status coaching notification when the user fitness goal is achievable during the current period. The status coaching notification may include a first textual message when the current progress is less than the historical progress and a second textual message when the current progress is greater than the historical progress.

Figure 7:
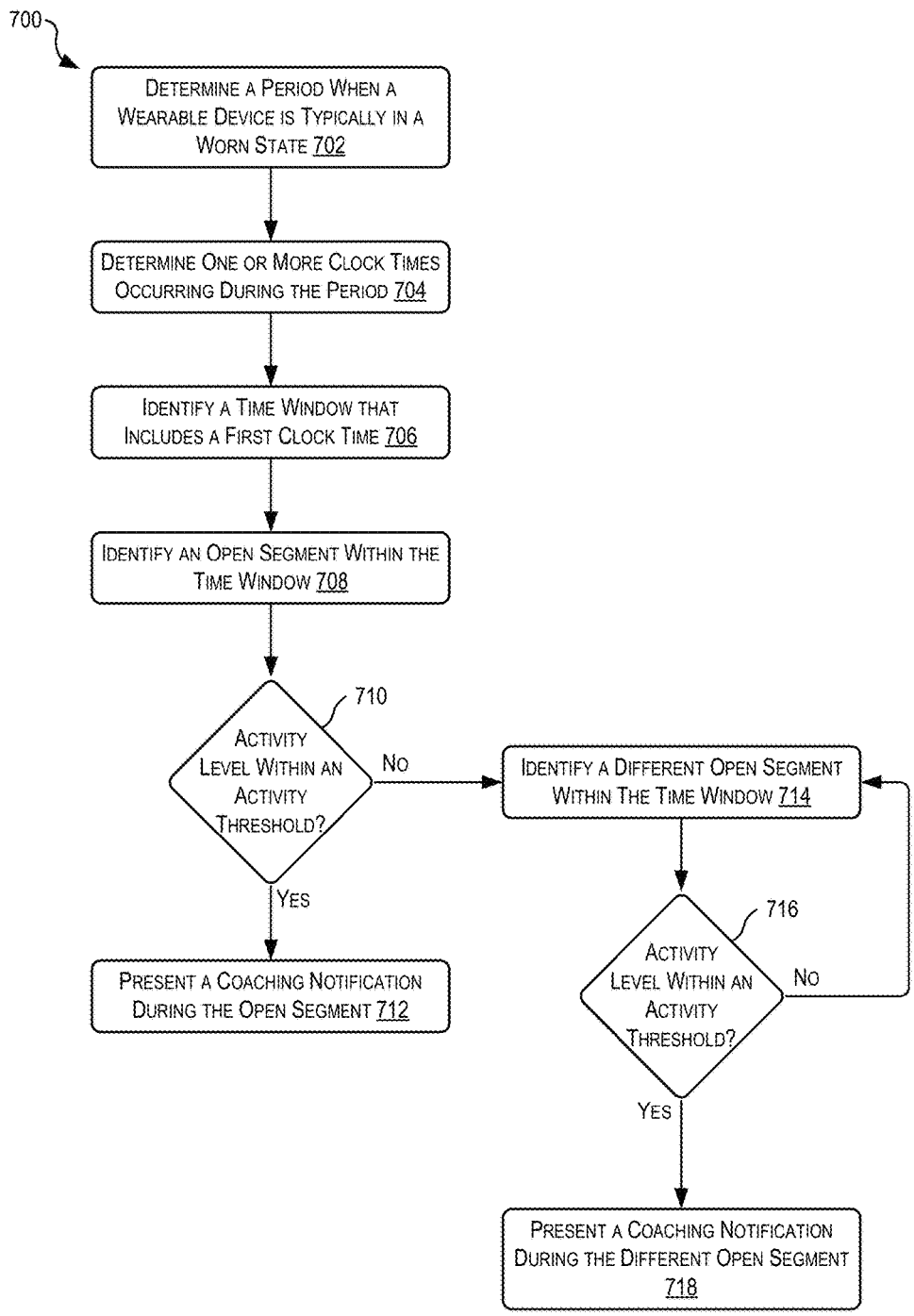
FIG. 7 illustrates a flowchart of a process for determining aspects of user coaching notifications, according to at least one example.

FIG. 7 depicts the process 700 including example acts or techniques relating to determining aspects of user coaching notifications, according to at least one example. The fitness module 810, whether embodied in the wearable electronic device 106, the user device 802, or the service provider computer 804, or any suitable combination of the foregoing may perform the process 700 of FIG. 7. The process 700 may begin at 702 by determining a period that a wearable device is typically in a worn state. In some examples, determining the period may be based at least in part on earlier periods of historical data representing the wearable device in the worn state.

At 704, the process 700 may include determining one or more clock times occurring during the period. In some example, determining the one or more clock times may be based at least in part on configuration information. The one or more clock times may be times during the period for scheduling the coaching notification. The configuration information may be generated in response to user input that indicates user preferences for receiving coaching notifications. For example, a user may indicate in a configuration file stored by a settings application on the wearable electronic device that the user would like to receive coaching notifications four times during the period. Based on this information and an estimated length of the period, the one or more clocks times occurring during the period may be determined (e.g., 9 am, 12 pm, 3 pm, and 6 pm).

At 706, the process 700 may include identifying a time window that includes a first clock time of the one or more clock times. The time window may be a time range that includes multiple minutes and the first clock time. For example, if the first clock time were 3 pm, the time window may range from 2:45 pm to 3:15 pm. In some examples, the time window may include a first block of time occurring before the first clock time and a second block of time occurring after the first clock time. In this example, the first block of time and the second block of time may be the same.

At 708, the process 700 may include identifying an open segment within the time window. Identifying the open segment may be based at least in part on user calendar data that is descriptive of a calendar associated with a user account. For example, if the time window ranged from 2:45 pm to 3:15 pm and the calendar data indicates that the user is in a meeting from 2:30 pm to 3:00 pm, the open segment may be identified as 3:00 pm to 3:15 pm. In some examples, the open segments are identified as smaller ranges of time such as 3:00 pm to 3:05 pm. In some examples, the open segment may be a block of time on the calendar of a user account that is free of appointments and meetings.

At 710, the process 700 may include determining whether an activity level is within an activity threshold. In some examples, determining whether the activity level is within the activity threshold may be based at least in part on activity data collected during the open segment. The activity level may be an activity level of the user. The activity data may include fitness data collected by the wearable electronic device from the user. For example, activity data may include heart rate data, perspiration data, and other similar user data. In some examples, the activity data may include other data that is indicative of the user being at a restful state. For example, the activity data may include absence of motion data detectable by sensors of the wearable electronic device.

If the answer at 710 is yes, the process 700 may proceed to 712 at which the process 700 may include presenting the coaching notification during the open segment. In some examples, the coaching notification may include a request to perform a breathing sequence. The breathing sequence, which may be led by a breathing application, may coach the user through the breathing sequence (e.g., a series of coordinated inhales and exhales). The coaching notification may include an option for beginning the breathing sequence. In this example, the process 700 may also include receiving selection information indicating user selection of the option. The process 700 may also include, in response to receiving the selection information, opening the breathing application to guide user action through the breathing sequence.

As the breathing sequence may be best performed with the user is free (e.g., as shown in the user's calendar or other by other data) and not otherwise active (e.g., as indicated by the activity data), the process 700 may determine an appropriate time for presenting the coaching notification given these constraints.

If the answer at 710 is no, the process 700 may proceed to 714 at which the process 700 may include identifying a different open segment within the time window. Identifying the different open segment may be performed in a manner similar to block 708.

At 716, the process, the process 700 may include determining whether an activity level is within an activity threshold. In some examples, determining whether the activity level is within the activity threshold may be based at least in part on activity data collected during the different open segment.

If the answer at 716 is no, the process 700 may return to 714 to identify another different open segment within the time window.

If the answer at 716 is yes, the process 700 may proceed to 718 at which the process 700 may include presenting the coaching notification during the different open segment. This may include presenting, at a display of the wearable electronic device, the coaching notification during the open segment when the activity level is within the activity threshold.

Figure 8:
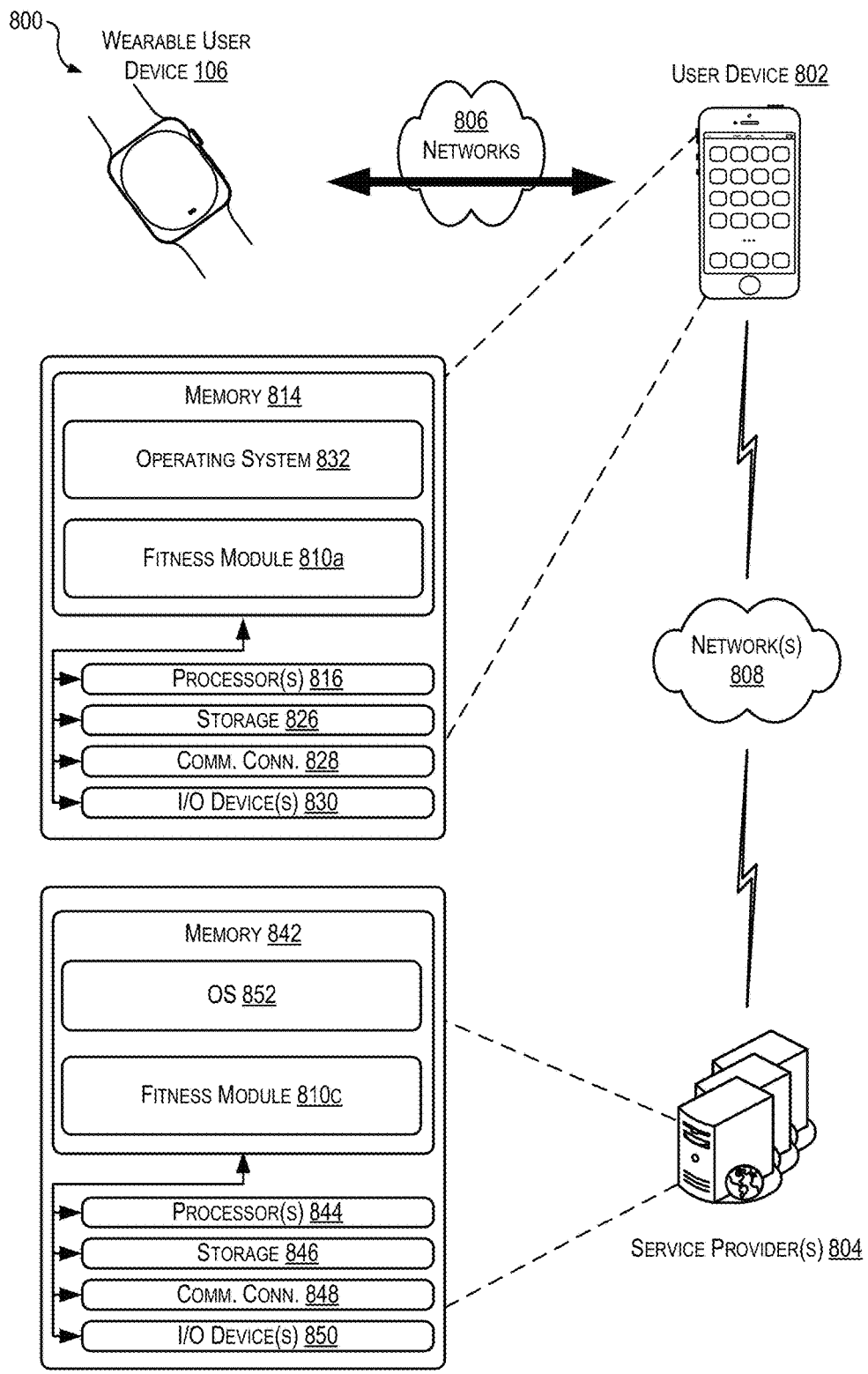
FIG. 8 illustrates a simplified block diagram depicting an example architecture for implementing techniques relating to determining aspects of user coaching notifications, according to at least one example.

FIG. 8 illustrates an example architecture or environment 800 configured to implement techniques relating to determining aspects of user coaching notifications, according to at least one example. In some examples, the example architecture 800 may further be configured to enable the user device 802, the service provider computers 804, and the wearable electronic device 106 to share information. In some examples, the devices may be connected via one or more networks 808 and/or 806 (e.g., via Bluetooth, WiFi, the Internet, or the like). In the architecture 800, one or more users may utilize the user device 802 to manage, control, or otherwise utilize the wearable electronic device 106, via the one or more networks 806. Additionally, in some examples, the wearable electronic device 106, the service provider computers 804, and the user device 802 may be configured or otherwise built as a single device. For example, the wearable electronic device 106 and/or the user device 802 may be configured to implement the examples described herein as a single computing unit, exercising the examples described above and below without the need for the other devices described.

In some examples, the networks 806, 808 may include any one or a combination of many different types of networks, such as cable networks, the Internet, wireless networks, cellular networks, satellite networks, other private and/or public networks, or any combination thereof. While the illustrated example represents the user device 802 accessing the service provider computers 804 via the networks 808, the described techniques may equally apply in instances where the user device 802 interacts with the service provider computers 804 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the user device 802 may be configured to collect and/or manage user activity data potentially received from the wearable electronic device 106. In some examples, the wearable electronic device 106 may be configured to provide health, fitness, activity, and/or medical data of the user to a third- or first-party application (e.g., the service provider 804). In turn, this data may be used by the user device 802 to schedule and present coaching notifications. Of course, the wearable electronic device 106 may also use the collected data to schedule and present coaching notifications as described herein. The user device 802 may be any type of computing device such as, but not limited to, a mobile phone, a smartphone, a personal digital assistant (PDA), a laptop computer, a desktop computer, a thin-client device, a tablet computer, a wearable device, or the like. In some examples, the user device 802 may be in communication with the service provider computers 804 and/or the wearable electronic device 106 via the networks 808, 806, or via other network connections.

In one illustrative configuration, the user device 802 may include at least one memory 814 and one or more processing units (or processor(s)) 816. The processor(s) 816 may be implemented as appropriate in hardware, computer-executable instructions, firmware, or combinations thereof. Computer-executable instruction or firmware implementations of the processor(s) 816 may include computer-executable or machine-executable instructions written in any suitable programming language to perform the various functions described. The user device 802 may also include geo-location devices (e.g., a global positioning system (GPS) device or the like) for providing and/or recording geographic location information associated with the user device 802. In some examples, the wearable user device 106 may also include geo-location devices for providing and/or recording geographic location information associated with wearable user device 106.

The memory 814 may store program instructions that are loadable and executable on the processor(s) 816, as well as data generated during the execution of these programs. Depending on the configuration and type of the user device 802, the memory 814 may be volatile (such as random access memory (RAM)) and/or non-volatile (such as read-only memory (ROM), flash memory, etc.). The user device 802 may also include additional removable storage and/or non-removable storage 826 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 814 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 814 and the additional storage 826, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 814 and the additional storage 826 are both examples of non-transitory computer storage media. Additional types of computer storage media that may be present in the user device 104 may include, but are not limited to, phase-change RAM (PRAM), SRAM, DRAM, RAM, ROM, Electrically Erasable Programmable Read-Only Memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 802. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 802 may also contain communications connection(s) 828 that allow the user device 802 to communicate with a data store, another computing device or server, user terminals, and/or other devices via the networks 808, 806. The user device 802 may also include I/O device (s) 830, such as a keyboard, a mouse, a pen, a voice input device, a touch input device, a display, speakers, a printer, etc.

Turning to the contents of the memory 814 in more detail, the memory 814 may include an operating system 832 and/or one or more application programs or services for implementing the features disclosed herein including a fitness module 810a. In some examples, the fitness module 810a may be configured to implement the features described herein. As described in detail with reference to later figures, the wearable user device 106 may include a memory that includes a similar fitness module 810b, which may be accessible by one or more processors of the wearable user device 106. The service provider 804 may also include a memory 842 that includes a fitness module 810c. In this manner, the techniques described herein may be implemented by any one, or a combination of more than one, of the computing devices (e.g., the wearable user device 106, the user device 802, or the service provider 804).

The service provider computers 804 may also be any type of computing device such as, but not limited to, a mobile phone, a smartphone, a PDA, a laptop computer, a desktop computer, a thin-client device, a tablet computer, a wearable device, a server computer, a virtual machine instance, etc. In some examples, the service provider computers 804 may be in communication with the user device 802 and/or the wearable user device 106 via the networks 808, 806, or via other network connections.

In one illustrative configuration, the service provider computers 804 may include at least one memory 842 and one or more processing units (or processor(s)) 844. The processor(s) 844 may be implemented as appropriate in hardware, computer-executable instructions, firmware, or combinations thereof. Computer-executable instruction or firmware implementations of the processor(s) 844 may include computer-executable or machine-executable instructions written in any suitable programming language to perform the various functions described.

The memory 842 may store program instructions that are loadable and executable on the processor(s) 844, as well as data generated during the execution of these programs. Depending on the configuration and type of service provider computer 804, the memory 842 may be volatile (such as RAM) and/or non-volatile (such as ROM, flash memory, etc.). The service provider computer 804 may also include additional removable storage and/or non-removable storage 846 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 842 may include multiple different types of memory, such as SRAM, DRAM, or ROM. While the volatile memory described herein may be referred to as RAM, any volatile memory that would not maintain data stored therein once unplugged from a host and/or power would be appropriate. The memory 842 and the additional storage 846, both removable and non-removable, are both additional examples of non-transitory computer-readable storage media.

The service provider computer 804 may also contain communications connection(s) 848 that allow the service provider computer 804 to communicate with a data store, another computing device or server, user terminals and/or other devices via the networks 808, 806. The service provider computer 804 may also include I/O device(s) 850, such as a keyboard, a mouse, a pen, a voice input device, a touch input device, a display, speakers, a printer, etc.

Turning to the contents of the memory 842 in more detail, the memory 842 may include an operating system 852 and/or one or more application programs or services for implementing the features disclosed herein including the fitness module 810c.

Figure 9:
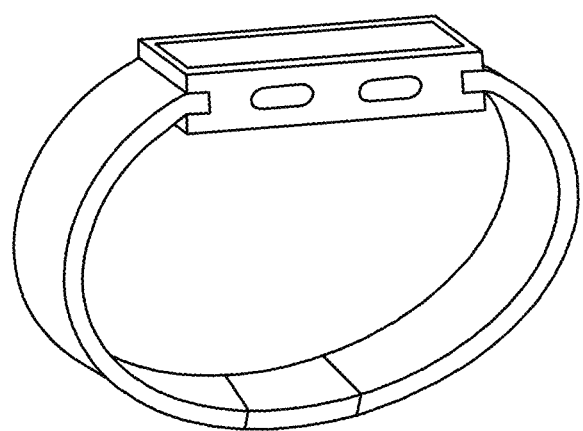
FIG. 9 illustrates an electronic device for implementing techniques relating to determining aspects of user coaching notifications, according to at least one example.

Examples described herein may take the form of, be incorporated in, or operate with a suitable wearable electronic device. One example of such a device is shown in FIG. 9 and takes the form of a wearable mechanism. As shown, the mechanism may be worn on a user's wrist and secured thereto by a band. The mechanism may have a variety of functions including, but not limited to: keeping time; monitoring a user's physiological signals and providing health-related information based at least in part on those signals; communicating (in a wired or wireless fashion) with other electronic devices, which may be different types of devices having different functionalities; providing alerts to a user, which may include audio, haptic, visual and/or other sensory output, any or all of which may be synchronized with one another; visually depicting data on a display; gather data form one or more sensors that may be used to initiate, control, or modify operations of the device; determine a location of a touch on a surface of the device and/or an amount of force exerted on the device, and use either or both as input; accepting voice input to control one or more functions; accepting tactile input to control one or more functions; and so on.

Alternative examples of suitable electronic devices include a phone; a tablet computing device; a portable media player; and so on. Still other suitable electronic devices may include laptop/notebook computers, personal digital assistants, touch screens, input-sensitive pads or surfaces, and so on.

In some examples the electronic device may accept a variety of bands, straps, or other retention mechanisms (collectively, "bands"). These bands may be removably connected to the electronic device by a lug that is accepted in a recess or other aperture within the device and locks thereto. The lug may be part of the band or may be separable (and/or separate) from the band. Generally, the lug may lock into the electronic device's recess and thereby maintain connection between the band and device. The user may release a locking mechanism to permit the lug to slide or otherwise move out of the recess. In some examples, the recess may be formed in the band and the lug may be affixed or incorporated into the device.

A user may change combinations of bands and electronic devices, thereby permitting mixing and matching of the two categories. It should be appreciated that devices having other forms and/or functions may include similar recesses and may releasably mate with a lug and/or band incorporating a lug. In this fashion, an ecosystem of bands and devices may be envisioned, each of which is compatible with another. A single band may be used to connect to devices, as one further example; in such examples the band may include electrical interconnections that permit the two devices to transmit signals to one another and thereby interact with one another.

In many examples, the electronic device may keep and display time, essentially functioning as a wristwatch among other things. Time may be displayed in an analog or digital format, depending on the device, its settings, and (in some cases) a user's preferences. Typically, time is displayed on a digital display stack forming part of the exterior of the device.

The display stack may include a cover element, such as a cover glass, overlying a display. The cover glass need not necessarily be formed from glass, although that is an option; it may be formed from sapphire, zirconia, alumina, chemically strengthened glass, hardened plastic and so on. Likewise, the display may be a liquid crystal display, an organic light-emitting diode display, or any other suitable display technology. Among other elements, the display stack may include a backlight in some examples.

The device may also include one or more touch sensors to determine a location of a touch on the cover glass. A touch sensor may be incorporated into or on the display stack in order to determine a location of a touch. The touch sensor may be self-capacitive in certain examples, mutual-capacitive in others, or a combination thereof.

Similarly, the device may include a force sensor to determine an amount of force applied to the cover glass. The force sensor may be a capacitive sensor in some examples and a strain sensor in other examples. In either example, the force sensor is generally transparent and made from transparent materials, or is located beneath or away from the display in order not to interfere with the view of the display. The force sensor may, for example, take the form of two capacitive plates separated by silicone or another deformable material. As the capacitive plates move closer together under an external force, the change in capacitance may be measured and a value of the external force correlated from the capacitance change. Further, by comparing relative capacitance changes from multiple points on the force sensor, or from multiple force sensors, a location or locations at which force is exerted may be determined. In one example the force sensor may take the form of a gasket extending beneath the periphery of the display. The gasket may be segmented or unitary, depending on the example.

The electronic device may also provide alerts to a user. An alert may be generated in response to: a change in status of the device (one example of which is power running low); receipt of information by the device (such as receiving a message); communications between the device and another mechanism/device (such as a second type of device informing the device that a message is waiting or communication is in progress); an operational state of an application (such as, as part of a game, or when a calendar appointment is imminent) or the operating system (such as when the device powers on or shuts down); and so on. The number and types of triggers for an alert are various and far-ranging.

The alert may be auditory, visual, haptic, or a combination thereof. A haptic actuator may be housed within the device and may move linearly to generate haptic output (although in alternative examples the haptic actuator may be rotary or any other type). A speaker may provide auditory components of an alert and the aforementioned display may provide visual alert components. In some examples a dedicated light, display, or other visual output component may be used as part of an alert.

The auditory, haptic, and/or visual components of the alert may be synchronized to provide an overall experience to a user. One or more components may be delayed relative to other components to create a desired synchronization among them. The components may be synchronized so that they are perceived substantially simultaneously; as one example, a haptic output may be initiated slightly before an auditory output since the haptic output may take longer to be perceived than the audio. As another example, a haptic output (or portion thereof) may be initiated substantially before the auditory output, but at a weak or even subliminal level, thereby priming the wearer to receive the auditory output.

Figure 10:
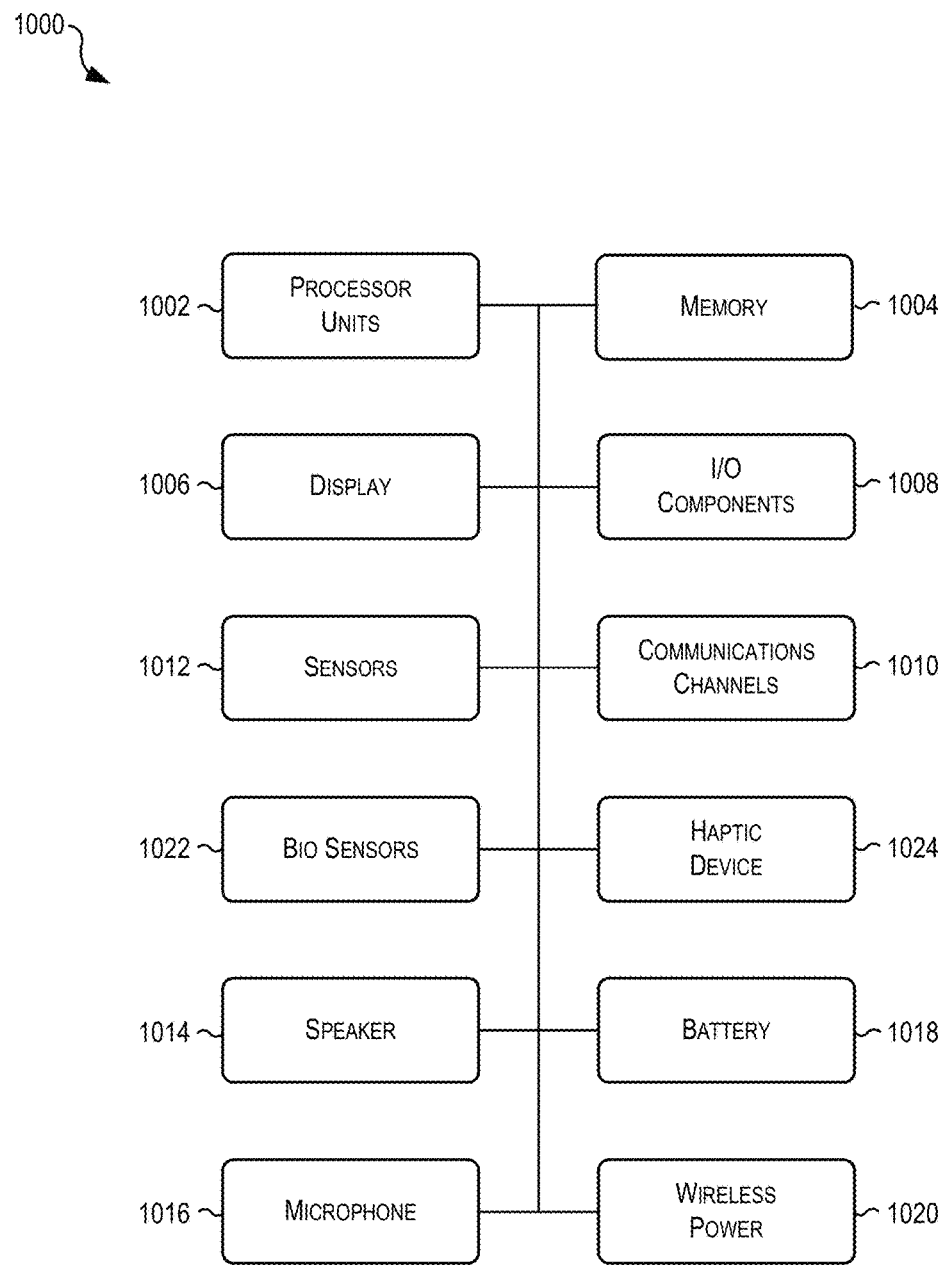
FIG. 10 illustrates a simplified block diagram including components of an example electronic device for implementing techniques relating to determining aspects of user coaching notifications, according to at least one example.

FIG. 10 depicts an example schematic diagram of a wearable electronic device 1000. The wearable electronic device 1000 is an example of the wearable user device 106. As shown in FIG. 10, the device 1000 includes one or more processing units 1002 that are configured to access a memory 1004 having instructions stored thereon.

The memory 1004, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 1004 is an example of non-transitory computer storage media. Additional types of computer storage media that may be present in the user device 104 may include, but are not limited to, phase-change RAM (PRAM), SRAM, DRAM, RAM, ROM, EEPROM, flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 1000. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The instructions or computer programs may be configured to perform one or more of the operations or functions described with respect to the device 1000 (e.g., the fitness module 810b). For example, the instructions may be configured to control or coordinate the operation of the various components of the device. Such components include, but are not limited to, display 1006, one or more input/output components 1008, one or more communication channels 1010, one or more sensors 1012, a speaker 1014, microphone 1016, a battery 1018, wireless power 1020, bio sensors 1022, and/or one or more haptic feedback devices 1024. In some examples the speaker and microphone may be combined into a single unit and/or may share a common port through a housing of the device.

The processing units 1002 of FIG. 10 may be implemented as any electronic device capable of processing, receiving, or transmitting data or instructions. For example, the processing units 1002 may include one or more of: a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

As shown in FIG. 10, the device 1000 may also include one or more acoustic elements, including a speaker 1014 and/or a microphone 1016. The speaker 1014 may include drive electronics or circuitry and may be configured to produce an audible sound or acoustic signal in response to a command or input. Similarly, the microphone 1016 may also include drive electronics or circuitry and is configured to receive an audible sound or acoustic signal in response to a command or input. The speaker 1014 and the microphone 1016 may be acoustically coupled to port or opening in the case that allows acoustic energy to pass, but may prevent the ingress of liquid and other debris.

Figure 11:
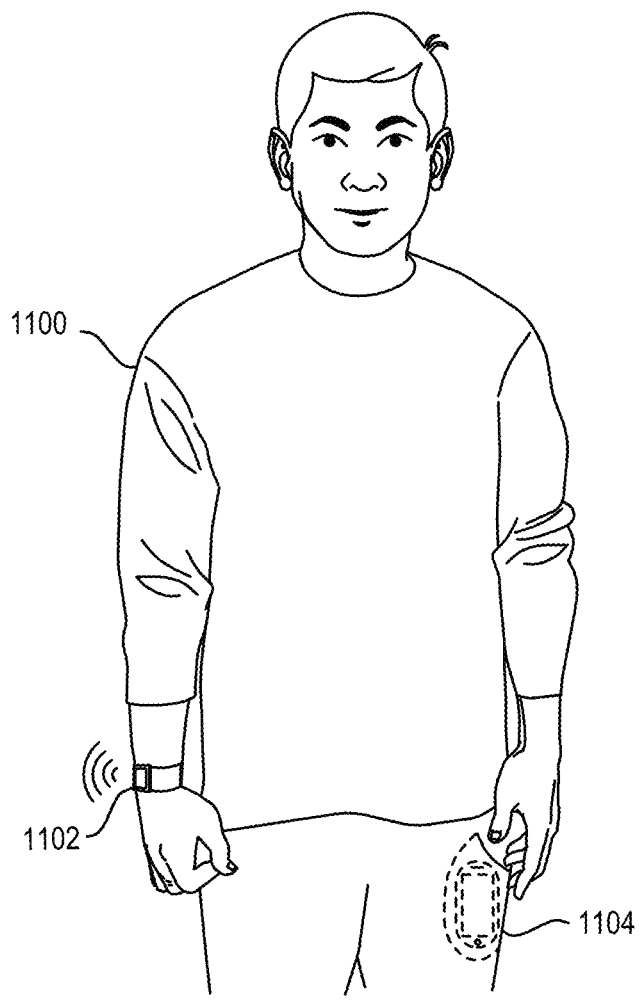
FIG. 11 illustrates a simplified diagram including example electronic devices for implementing techniques relating to determining aspects of user coaching notifications, according to at least one example.

The example electronic device may communicate with other electronic devices either through a wired connection or wirelessly. Data may be passed between devices, permitting one device to relay information to another; control another; employ another's sensors, outputs, and/or inputs; and so on. FIG. 11 depicts a user 1100 wearing a first electronic device 1102 with a second electronic device 1104 in his pocket. Data may be wirelessly transmitted between the electronic devices 1102, 1104, thereby permitting the user 1100 to receive, view, and interact with data from the second device 1104 by means of the first electronic device 1102. Thus, the user 1100 may have access to part or all of the second device's functionality through the first electronic device 1102 without actually needing to interact directly with the second device 1104. In some examples, the second electronic device 1104 may be an example of the user device 804. The first electronic device 1102 may be an example of the wearable user device 106.

Further, the electronic devices 1102, 1104 may cooperate not only to share data, but to share functionality as well. For example, one of the two devices may incorporate a sensor, application, or function that the other lacks. The electronic device lacking such capabilities may request them from the other device, which may share wirelessly with the requesting device. Thus, multiple devices may operate together to provide expanded functions, software, access, and the like between the two and ultimately to a user. As one non-limiting example, the electronic device 1102 may be unable to place or receive telephone calls while the second device 1104 may be able to do so. A user may nonetheless make and/or receive calls through the first device 1102, which may employ the second device 1104 to actually place or accept a call.

As another non-limiting example, an electronic device 1102 may wirelessly communicate with a sales terminal nearby, thus permitting a user to quickly and efficiently conduct a transaction such as selling, buying, or returning a good. The electronic device may use near field communications technology to perform these and other functions.

As mentioned above, a band may be connected to two electronic devices and may serve as a wired communication path between the two. As another example, the devices may communicate wirelessly, thereby permitting one device to relay information from a second to a user. This latter example may be particularly useful when the second is inaccessible.

Certain examples may incorporate one or more biometric sensors to measure certain physiological characteristics of a user. The device may include a photoplesymogram sensor to determine a user's heart rate or blood oxygenation levels, for example. The device may also or instead include electrodes to measure the body impedance of a user, which may permit the device to estimate body fat percentages, the body's electrical activity, body impedance, and so on. Also include blood pressure, ultraviolet exposure, etc. Depending on the sensors incorporated into or associated with the electronic device, a variety of user characteristics may be measured and/or estimated, thereby permitting different health data to be provided to a user. In some examples, the sensed biometric data may be used, in part, to determine the historic, current, and/or predicted activity data of the user.

Certain examples may be wirelessly charged. For example, an inductive charging base may transmit power to an inductive receiver within the device in order to charge a battery of the device. Further, by varying the inductive field between the device and base, data may be communicated between the two. As one simple non-limiting example, this may be used to wake the base from a low-power sleep state to an active charging state when the device is placed on the base. Other wireless charging systems may also be used (e.g., near field magnetic resonance and radio frequency). Alternatively, the device may also employ wired charging through electrodes.

In certain examples, the device may include a rotary input, which may take the form of a crown with a stem. The crown and stem may be rotated to provide the rotary input. Rotation of the stem and/or crown may be sensed optically, electrically, magnetically, or mechanically. Further, in some examples the crown and stem may also move laterally, thereby providing a second type of input to the device.

The electronic device may likewise include one or more buttons. The button(s) may be depressed to provide yet another input to the device. In various examples, the button may be a dome switch, rocker switch, electrical contact, magnetic switch, and so on. In some examples the button may be waterproof or otherwise sealed against the environment.

Various examples may include or otherwise incorporate one or more motion sensors. A motion sensor may detect motion of the device and provide, modify, cease, or otherwise affect a state, output, or input of the device or associated applications based at least in part on the motion. As non-limiting examples, a motion may be used to silence the device or acknowledge an alert generated by the device. Sample motion sensors include accelerometers, gyroscopic sensors, magnetometers, GPS sensors, distance sensors, and so on. Some examples may use a GPS sensor to facilitate or enable location and/or navigation assistance.

Certain examples may incorporate an ambient light sensor. The ambient light sensor may permit the device to sense a brightness of its environment and adjust certain operational parameters accordingly. For example, the electronic device may modify a brightness of a display in response to the sensed ambient light. As another example, the electronic device may turn the display off if little or no light is sensed for a period of time.

These and other functions, operations, and abilities of the electronic device will be apparent upon reading the specification in its entirety.

Certain examples of a wearable electronic device may include one or more sensors that can be used to calculate a health metric or other health-related information. As one example, a wearable electronic device may function as a wearable health assistant that provides health-related information (whether real-time or not) to the user, authorized third parties, and/or an associated monitoring device.

Figure 12:
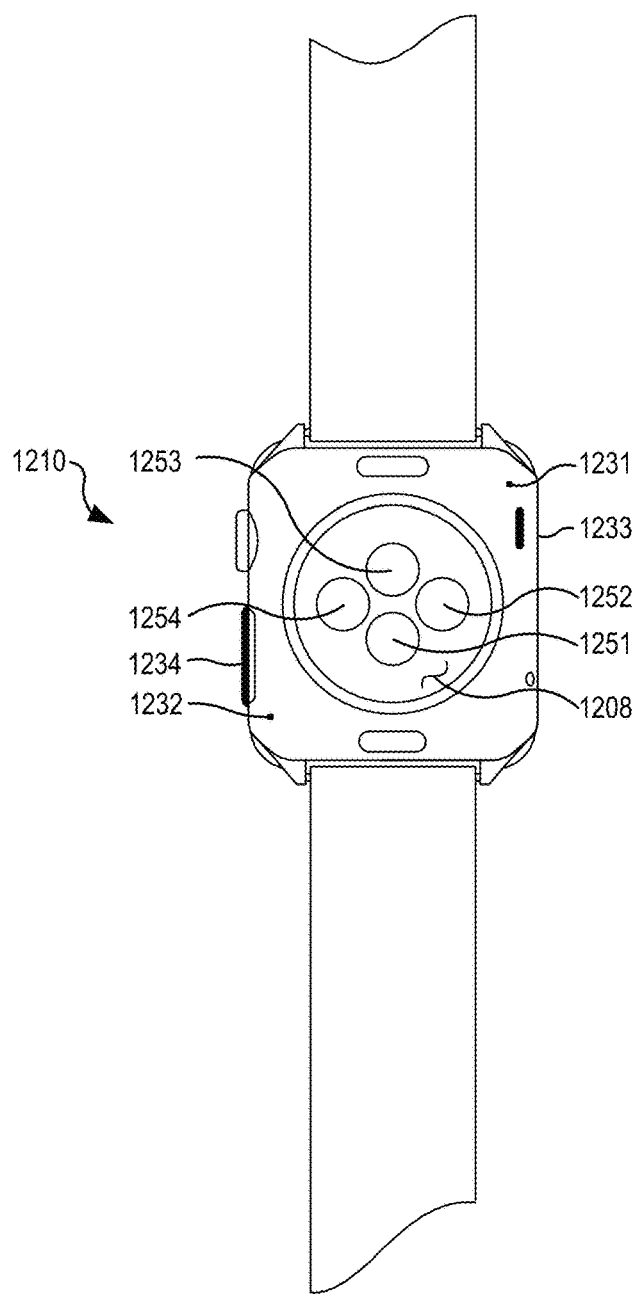
FIG. 12 illustrates an example electronic device for implementing techniques relating to determining aspects of user coaching notifications, according to at least one example.

FIG. 12 depicts an example electronic device 1200 having one or more biometric sensors. The electronic device 1200 is an example of the wearable user device 106. As shown in FIG. 12, an array of light sources and a photodetector 1251-1254 may be disposed on the rear surface of the device 1200. In one example, the light sources 1251-1253 are formed from light emitting diode (LED) elements that are configured to emit light into a portion of the wearer's body (e.g., wrist). The photodetector 1254 is shared between the multiple light sources 1251-1253 and is configured to receive light reflected from the body. The photodetector may be formed from a photodiode material that is configured to produce a signal based at least in part on the received light. In one implementation, the signal produced by the photodetector 1254 is used to compute a health metric associated with the wearer. In some cases, the light sources 1251-1253 and the photodetector 1254 form a photoplethysmography (PPG) sensor. The first light source 1251 may include, for example, a green LED, which may be adapted for detecting blood perfusion in the body of the wearer. The second light source 1252 may include, for example, an infrared LED, which may be adapted to detect changes in water content or other properties of the body. The third 1253 light source may be a similar type or different types of LED element, depending on the sensing configuration. The optical (e.g., PPG) sensor or sensors may be used to compute various health metrics, including, without limitation, a heart rate, a respiration rate, blood oxygenation level, a blood volume estimate, blood pressure, or a combination thereof. One or more of the light sources 1251-1253 and the photodetector 1254 may also be used for optical data transfer with a base or other device. While FIG. 12 depicts one example, the number of light sources and/or photodetectors may vary in different examples. For example, another example may use more than one photodetector. Another example may also use fewer or more light sources than are depicted in the example of FIG. 12.

Also as shown in FIG. 12, the device 1200 includes multiple electrodes 1231, 1232, 1233, 1234 that are located on or near external surfaces of the device 1200. In the present example, the device 1200 includes a first electrode 1231 and a second electrode 1232 that are located on or proximate to a rear-facing surface of the device body 1210. In this example, the first electrode 1231 and the second electrode 1232 are configured to make electrical contact with the skin of the user wearing the device 1200. In some cases, the first 1231 and second 1232 electrodes are used to take an electrical measurement or receive an electrical signal from the body of the user. As also shown in FIG. 12, the device 1200 may include a third electrode 1233 and a fourth electrode 1234 that are located on or proximate to a perimeter of the case of the device body 1210. In the present example, the third 1233 and fourth 1234 electrodes are configured to be contacted by one or more fingers of the user who is wearing or interacting with the device 1200. In some cases, the third 1233 and fourth 1234 electrodes are also used to take an electrical measurement or receive an electrical signal from the body of the user. In some cases, the first 1231, second 1232, third 1233, and fourth 1234 electrodes are all used to take a measurement or series of measurements that can be used to compute another health metric of the user's body. Health metrics that may be computed using the electrodes include, without limitation, heart functions (ECG, EKG), water content, body-fat ratios, galvanic skin resistance, and combinations thereof.

In the configuration depicted in FIG. 12, the electronic device 1200 includes one or more apertures in the case 1210. A light source 1251-1254 may be disposed in each aperture. In one example, each light source 1251-1253 is implemented as a light-emitting diode (LED). In the present example, the four apertures, three light sources 1251-1253, and a single detector 1254 are used to form one or more sensors. Other examples can include any number of light sources. For example, two light sources can be used in some examples.

The light sources may operate at the same light wavelength range, or the light sources can operate at different light wavelength ranges. As one example, with two light sources one light source may transmit light in the visible wavelength range while the other light source can emit light in the infrared wavelength range. With four light sources, two light sources may transmit light in the visible wavelength range while the other two light sources can emit light in the infrared wavelength range. For example, in one example, at least one light source can emit light in the wavelength range associated with the color green while another light source transmits light in the infrared wavelength range. When a physiological parameter of the user is to be determined, the light sources emit light toward the user's skin and the optical sensor senses an amount of reflected light. In some cases, a modulation pattern or sequence may be used to turn the light sources on and off and sample or sense the reflected light.

Illustrative methods and systems for managing user device connections are described above. Some or all of these systems and methods may, but need not, be implemented at least partially by architectures such as those shown at least in FIGS. 1-12. While many of the examples are described above with reference to personal, activity, and/or health-related information, it should be understood that any type of user information or non-user information (e.g., data of any type) may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various examples further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most examples utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In examples utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of examples, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate examples may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various examples.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
accessing, by a fitness application of a wearable device having an associated user account, historical fitness data associated with the user account, the historical fitness data collected by the wearable device during a plurality of days that together define a historical period;
detecting a beginning of a current day based at least in part on a detected user action performed at the wearable device, the current day comprising a plurality of segments;
determining whether to present a coaching notification at a conclusion of a first segment of the plurality of segments by at least:
accessing current fitness data collected by the wearable device and tracked by the fitness application during the first segment;
comparing the current fitness data to the historical fitness data to identify a correlation between a current progress toward a fitness goal and a historical progress toward the fitness goal; and
determining, based at least in part on the correlation, whether the fitness goal is achievable during one or more other segments of the plurality of segments; and
presenting a coaching notification at the conclusion of the first segment when the fitness goal is achievable during the one or more other segments, the coaching notification identifying the fitness goal.

2. The computer-implemented method of claim 1, wherein the coaching notification indicates the current progress toward the fitness goal.

3. The computer-implemented method of claim 1, further comprising determining an estimated conclusion of the current day based at least in part on the historical fitness data, and wherein the coaching notification comprises a suggested action for achieving the fitness goal prior to the estimated conclusion of the current day.

4. The computer-implemented method of claim 1, wherein the fitness goal comprises at least one of a stand goal, a caloric burn goal, or a move goal.

5. The computer-implemented method of claim 1, wherein each segment of the plurality of segments is equivalent.

6. A wearable device, comprising:
a display;
a memory configured to store computer-executable instructions; and
a processor configured to access the memory and execute the computer-executable instructions to collectively at least:
access historical fitness data collected during a plurality of periods that together define a historical period;
access current fitness data collected during a first segment of a current period;
determine a correlation between a current progress toward a user fitness goal and a historical progress toward the user fitness goal based at least in part on the historical fitness data and the current data; and
present, at the display, a coaching notification at a conclusion of the first segment when the correlation indicates the user fitness goal is achievable during one or more other segments of the current period.

7. The wearable device of claim 6, wherein each period is a day and the historical period is a month.

8. The wearable device of claim 6, wherein the historical fitness data is collected while the wearable device is in a worn state.

9. The wearable device of claim 6, wherein the processor is further configured to access the memory and execute the computer-executable instructions to collectively at least:
determine an estimated conclusion of the current period based at least in part on the historical fitness data;
determine, based at least in part on the current fitness data, whether a current fitness value associated with the user fitness goal exceeds a threshold;
when the current fitness value exceeds the threshold, determine a second coaching notification based at least in part on the current fitness data, the second coaching notification identifying the user fitness goal and including a suggested action for achieving the user fitness goal prior to the estimated conclusion of the current period; and
present, at the display, the second coaching notification prior to the estimated conclusion of the current period.

10. The wearable device of claim 9, wherein determining the second coaching notification is further based at least in part on user biometric information.

11. The wearable device of claim 9, wherein presenting the second coaching notification comprises presenting the second coaching notification after presenting the coaching notification.

12. The wearable device of claim 6, wherein the first segment corresponds to 25% of the current period or 75% of the current period.

13. The wearable device of claim 6, wherein the processor is further configured to access the memory and execute the computer-executable instructions to collectively at least determine an estimated conclusion of the current period based at least in part on the historical fitness data, and wherein the coaching notification comprises a suggested action for achieving the user fitness goal prior to the estimated conclusion of the current period.

14. The wearable device of claim 13, wherein the suggested action is walking for a fixed period of time.

15. The wearable device of claim 6, wherein the coaching notification comprises an option for beginning a workout, and wherein the processor is further configured to access the memory and execute the computer-executable instructions to collectively at least:
receive information indicating user selection of the option;
in response to receiving the information, initiate the workout; and
collect additional current fitness data during the workout.

16. A computer-implemented method, comprising:
accessing, by a fitness application of a wearable device, historical user fitness data, the historical fitness data collected by the wearable device during a plurality of periods that together define a historical period;
determining an estimated conclusion of a current period based at least in part on the historical fitness data;
accessing current fitness data collected by the wearable device and tracked by the fitness application during the current period;
determining, based at least in part on the current fitness data, whether a current fitness value associated with a user fitness goal exceeds a threshold;
when the current fitness value exceeds the threshold, determining a coaching notification based at least in part on the current fitness data, the coaching notification identifying the user fitness goal and including a suggested action for achieving the user fitness goal prior to the estimated conclusion of the current period; and presenting the coaching notification.

17. The computer-implemented method of claim 16, further comprising determining whether the user fitness goal is achievable within a remaining portion of the current period, and wherein determining the coaching notification comprises determining the coaching notification when the user fitness goal is achievable within the remaining portion of the current period.

18. The computer-implemented method of claim 16, wherein the coaching notification is a threshold coaching notification, and wherein the method further comprises:

comparing the current fitness data to the historical fitness data to identify a correlation between a current progress toward the user fitness goal and a historical progress toward the user fitness goal;

determining, based at least in part on the correlation, whether the user fitness goal is achievable during the current period; and prior to presenting the threshold coaching notification, presenting a status coaching notification when the user fitness goal is achievable during the current period.

19. The computer-implemented method of claim 18, wherein the status coaching notification includes a first textual message when the current progress is less than the historical progress and a second textual message when the current progress is greater than the historical progress.

20. The computer-implemented method of claim 16, wherein the historical fitness data comprises a user fitness profile with respect to the historical period.

* * * * *

UNITED STATES PATENT AND TRADEMARK OFFICE
CERTIFICATE OF CORRECTION

PATENT NO. : 10,194,418 B2  
APPLICATION NO. : 15/705802  
DATED : January 29, 2019  
INVENTOR(S) : Jay Kriz Blahnik et al.

Page 1 of 1

It is certified that error appears in the above-identified patent and that said Letters Patent is hereby corrected as shown below:

On the Title Page

In item (72) Inventors: Please add -- Kevin M. Lynch, Woodside, CA (US) -- after "Keith P. Avery, Sunnyvale, CA (US)"

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*